US009546994B2

(12) United States Patent
Rathmann et al.

(10) Patent No.: US 9,546,994 B2
(45) Date of Patent: Jan. 17, 2017

(54) BIOMARKERS FOR TYPE 2 DIABETES

(71) Applicants: Helmholtz Zentrum Munchen—Deutsches Forschungszentrum fur Gesundheit und Umwelt (GmbH), Neuherberg (DE); Deutsche Diabetes-Forschungsgesellschaft e.V.—Trager des Deutschen Diabetes-Zentrums Dusseldorf, Dusseldorf (DE); Eberhard Karls Universitat Tubingen, Medizinische Fakultat, Tubingen (DE)

(72) Inventors: Wolfgang Rathmann, Essen (DE); Christian Herder, Dusseldorf (DE); Thomas Illig, Hannover (DE); Jerzy Adamski, Munich (DE); Rui Wang-Sattler, Munich (DE); Zhongao Yu, Munich (DE); H.-Erich Wichmann, Neuherberg (DE); Hans-Ulrich Haring, Stuttgart (DE); Michael Roden, Vienna (AT); Annette Peters, Munich (DE); Christine Meisinger, Aichach (DE); Martin Hrabe De Angelis, Starnberg (DE); Thomas Meitinger, Munich (DE)

(73) Assignees: Helmholtz Zentrum Munchen-Deutsches Forschungszentrum fur Geseundheit und Umwelt (GmbH), Neuherberg (DE); Deutsche Diabetes-Forschungsgesellschaft e.V.—Trager des Deutschen Diabetes-Zentrums Dusseldorf, Dusseldorf (DE); Eberhard Karls Universitat Tubingen, Medizinische Fakultat, Tubingen (DE)

( * ) Notice: Subject to any disclaimer, the term of this patent is extended or adjusted under 35 U.S.C. 154(b) by 0 days.

(21) Appl. No.: 14/421,637

(22) PCT Filed: Aug. 13, 2013

(86) PCT No.: PCT/EP2013/066914
§ 371 (c)(1),
(2) Date: Feb. 13, 2015

(87) PCT Pub. No.: WO2014/026991
PCT Pub. Date: Feb. 20, 2014

(65) Prior Publication Data
US 2015/0204839 A1   Jul. 23, 2015

(30) Foreign Application Priority Data

Aug. 13, 2012  (EP) .................... 12180300

(51) Int. Cl.
*G01N 33/92* (2006.01)
*G01N 33/487* (2006.01)
(Continued)

(52) U.S. Cl.
CPC ............ *G01N 33/487* (2013.01); *G01N 24/08* (2013.01); *G01N 30/02* (2013.01);
(Continued)

(58) Field of Classification Search
None
See application file for complete search history.

(56) References Cited

U.S. PATENT DOCUMENTS 4,946,778 A   8/1990 Ladner et al.
6,080,560 A   6/2000 Russell et al.
(Continued)

FOREIGN PATENT DOCUMENTS

CN        102460160         5/2012
WO    WO 2010/114897 A1   10/2010

OTHER PUBLICATIONS

Wang, C. et al. Plasma Phospholipid Metabolic Profiling and Biomarkers of Type 2 Diabetes . . . Anal Chem 77(13)4108-4116, Jul. 1, 2005.*

(Continued)

*Primary Examiner* — Ralph Gitomer
(74) *Attorney, Agent, or Firm* — Mueting, Raasch & Gebhardt, P.A.

(57) ABSTRACT

The present invention relates to a method of identifying a predisposition for developing type 2 diabetes mellitus in a subject, said method comprising the step of assessing in a sample obtained from said subject the amount of one or more metabolite(s) selected from (a) a first group comprising the metabolites glycine, lysoPhosphatidylcholine acyl C18:2, lysoPhosphatidylcholine acyl C17:0, lysoPhosphatidylcholine acyl C18:0, lysoPhosphatidylcholine acyl C18:1, phosphatidylcholine acyl-alkyl C34:2, phosphatidylcholine acyl-alkyl C36:2, phosphatidylcholine acyl-alkyl C36:3 and isobaric metabolites having the same molecular mass as glycine, lysoPhosphatidylcholine acyl C18:2, lysoPhosphatidylcholine acyl C17:0, lysoPhosphatidylcholine acyl C18:0, lysoPhosphatidylcholine acyl C18:1, phosphatidylcholine acyl-alkyl C34:2, phosphatidylcholine acyl-alkyl C36:2 or phosphatidylcholine acyl-alkyl C36:3 but different chemical formula; and/or (b) a second group comprising the metabolite acetylcarnitine C2 and an isobaric metabolite having the same molecular weight as acetylcarnitine C2 but different chemical formula; wherein a decrease in the amount of a metabolite selected from said first group or an increase in the amount of a metabolite selected from said second group as compared to the amount of the corresponding metabolite(s) of a control is indicative of a predisposition to develop type 2 diabetes mellitus. Further, the invention relates to a method of identifying a compound capable of preventing (Continued)

Figure 1:
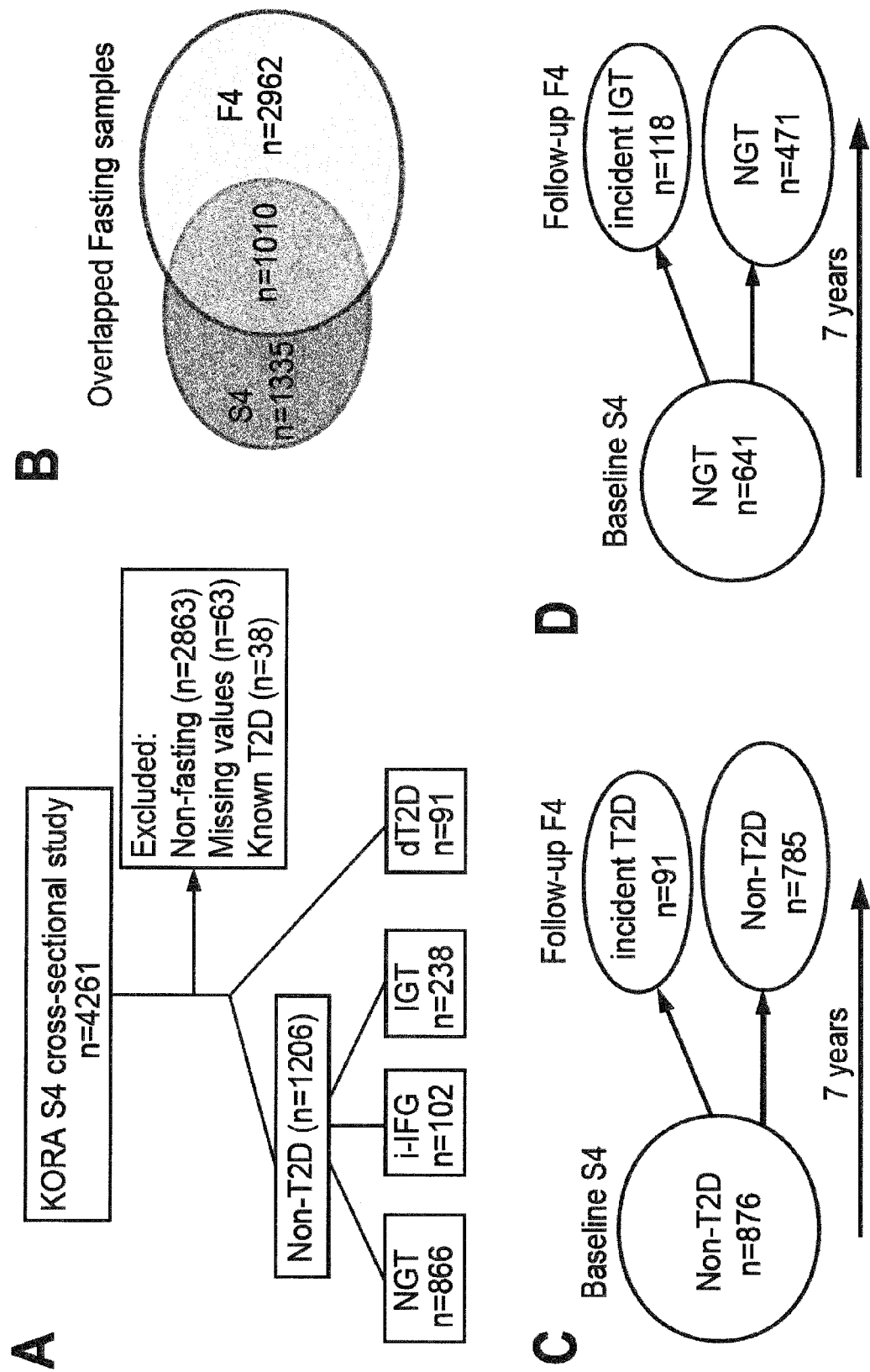

type 2 diabetes mellitus and diseases associated therewith or serving as a lead compound for developing a compound capable of preventing type 2 diabetes mellitus and diseases associated therewith and a method of selecting a therapy to prevent type 2 diabetes mellitus. Also, the invention relates to a kit.

7 Claims, 4 Drawing Sheets

(51) Int. Cl.
    *G01N 33/68* (2006.01)
    *G01N 24/08* (2006.01)
    *G01N 30/02* (2006.01)
    *G01N 30/72* (2006.01)
    *G01N 33/49* (2006.01)

(52) U.S. Cl.
    CPC ......... *G01N 30/7206* (2013.01); *G01N 33/49* (2013.01); *G01N 33/6893* (2013.01); *G01N 33/92* (2013.01); *G01N 2030/025* (2013.01); *G01N 2030/027* (2013.01); *G01N 2500/10* (2013.01); *G01N 2800/042* (2013.01); *G01N 2800/50* (2013.01)

(56) References Cited

U.S. PATENT DOCUMENTS

| | | | | |
|---|---|---|---|---|
| 2012/0122981 | A1* | 5/2012 | Hu | G01N 33/5038 514/560 |
| 2012/0129265 | A1 | 5/2012 | Lundin et al. | |
| 2013/0338031 | A1* | 12/2013 | Hu | G01N 33/6893 506/9 |

OTHER PUBLICATIONS

Wang-Settler, R. et al. Novel Biomarkers for Prediabetes Identified by Metabolomics. Molecular Systems Biology 1-11, Sep. 25, 2012.*
Adams et al., "Comprehensive plasma acylcarnitine profiles of type 2 diabetic and non-diabetic subjects with or without an uncoupling protein 3 (UCP3) missense polymorphism," *The FASEB Journal*, Mar. 2008; 22 (Meeting Abstract Supplement), 614.15.
Aschner, "Metabolic syndrome as a risk factor for diabetes," *Expert Rev. Cardiovasc. Ther.*, 2010, 8(3):407-412.
Berry et al., "A prototype computer systems for de novo protein design," *Biochemical Society Transactions*, 1994, 22:1033-1036.
Boeing et al., "EPIC—Germany—A Source for Studies into Diet and Risk of Chronic Diseases," *Annals of Nutrition & Metabolism*, 1999, 43:195-204.
Buijsse et al., "Risk Assessment Tools for Identifying Individuals at Risk of Developing Type 2 Diabetes," *Epidemiologic Reviews*, May 2011, 33:46-62.
Chiang, "Bile Acid Regulation of Gene Expression: Roles of Nuclear Hormone Receptors," *Endocrine Reviews*, Aug. 2002, 23(4):443-463.
Ciccimaro et al., "Stable-isotope dilution LC-MS for quantitative biomarker analysis," *Bioanalysis*, Feb. 2010, 2(2):311-341.
Curatolo et al., "Phase Behavior of Carbamyloxyphosphatidylcholine, a Sphingolipid Analogue," *Journal of Pharmaceutical Sciences*, Dec. 1985, 74(12):1255-1258.
Dagan et al., "Synthetic, non-natural sphingolipid analogs inhibit the biosynthesis of cellular sphingolipids, elevate ceramide and induce apoptotic cell death," *Biochimica et Biophysica Acta*, 2003, 1633:161-169.
Dörner et al., "The Synthesis of Peptidomimetic Combinatorial Libraries Through Successive Amide Alkylations," *Bioorganic & Medicinal Chemistry*, 1996, 4(5):709-715.

Elbashir et al., "Functional anatomy of siRNAs for mediating efficient RNAi in *Drosophila melanogaster* embryo lysate," *The EMBO Journal*, 2001, 20(23):6877-6888.
Executive Summary, "Standards of Medical Care in Diabetes—2010," *Diabetes Care*, Jan. 2010, 33(1):4-10.
Fassina et al., "Identification of Interactive Sites of Proteins and Protein Receptors bt Computer-Assisted Searches for Complementary Peptide Sequences," *Immunomethods*, 1994, 5:114-120.
Fiehn et al., "Plasma Metabolomics Profiles Reflective of Glucose Homeostasis in Non-Diabetic and Type 2 Diabetic Obese African-American Women," *PLoS ONE*, Dec. 2010, 5(12):1-10.
Figeys et al., "Protein Identification by Capillary Zone Electrophoresis/Microelectrospray Ionization-Tandem Mass Spectrometry at the Subfemtomole Level," *Anal. Chem.*, 1996, 68:1822-1828.
Gerich, "Type 2 Diabetes Mellitus is Associated with Multiple Cardiometabolic Risk Factors," *Clinical Cornerstone*, 2007, 8(3):53-68.
Griffiths et al. "Targeted Metabolomics for Biomarker Discovery," *Agnew. Chem. Int. Ed.*, 2010, 49:5426-5445.
Grundy, "Pre-Diabetes, Metabolic Syndrome, and Cardiovascular Risk," *Journal of the American College of Cardiology*, Feb. 2012, 59(7):635-643.
Ha et al., "The association of specific metabolites of lipid metabolism with markers of oxidative stress, inflammation and arterial stiffness in men with newly diagnosed type 2 diabetes," *Clinical Endocrinology*, 2012, 76:674-682.
Holle et al., KORA—A Research Platform for Population Based Health Research,: *Gesundheitswesen*, 2005, 67(1):19-25.
Holzgrabe et al., "Antibiotische Chemotherapeutika," *Deutsche Apotheker Zeitung*, Feb. 2000, 140:813-823.
Hunt et al., "Protein sequencing by tandem mass spectrometry," *Proc. Natl. Acad. Sci.*, Sep. 1986, 83:6233-6237.
Illig, et al., "A genome-wide perspective of genetic variation in human metabolism," *Nature Genetics*, Feb. 2010, 42(2):137-143.
International Search Report and Written Opinion, Jan. 2, 2014, PCT Patent Application No. PCT/EP2013/066914, 18 pgs.
Jones et al., "Deletion of PPARγ in adipose tissues of mice protects against high fat diet-induced obesity and insulin resistance," *PNAS*, Apr. 2005, 102(17):6207-6212.
Jourdan et al., "Body Fat Free Mass IS Associated with the Serum Metabolite Profile in a Population-Based Study," *PLoSOne*, Jun. 2012, 7(6):1-12.
Koal et al., "Challenges in Mass Spectrometry Based Targeted Metabolomics," *Current Molecular Medicine*, 2010, 10:216-226.
Köhler et al., "Continuous cultures of fused cells secreting antibody of predefined specificity," *Nature*, Aug. 1975, 256:495-497.
Koletzko et al., "The use of stable isotope techniques for nutritional and metabolic research in paediatrics," *Early Human Development*, 1998, 53:77-97.
Kozbor et al., "The production of monoclonal antibodies from human lymphocytes," *Immunology Today*, 1983, 4(3):72-79.
Kushnir et al., "Liquid chromatography tandem mass spectrometry for analysis of steroids in clinical laboratories," *Clinical Biochemistry*, 2011, 44:77-88.
Lechleitner, "Obesity and the Metabolic Syndrome in the Elderly—A Mini-Review," *Gerontology*, 2008, 54:253-259.
Lee et al., "Tracer-based metabolomics: Concepts and practices," *Clinical Biochemistry*, 2010, 43: 1269-1277.
Lloyd et al., "Childhood obesity and risk of the adult metabolic syndrome: a systematic review," *International Journal of Obesity*, 2012, 36:1-11.
Lyssenko et al., "Clinical Risk Factors, DNA Variants, and the Development of Type 2 Diabetes," *The New England Journal of Medicine*, Nov. 2008, 359(21):2220-2232.
Makishima, "Nuclear Receptors as Targets for Drug Development: Regulation of Cholesterol and Bile Acid Metabolism by Nuclear Receptors," *Journal of Pharmacological Sciences*, 2005, 97:177-183.
Malmborg et al., "BIAcore as a tool in antibody engineering," *Journal of Immunological Methods*, 1995, 183:7-13.
McGarry, "Dysregulation of Fatty Acid Metabolism in the Etiology of Type 2 Diabetes," *Diabetes*, Jan. 2002, 51:7-18.

(56) References Cited

OTHER PUBLICATIONS

Meisinger et al., "Prevalence of undiagnosed diabetes and impaired glucose regulation in 35-59-year-old individuals in Southern Germany: the KORA F4 Study," *DiabeticMedicine*, 2010, 27:360-362.
Melani et al., "Inhibition of Proliferation by c-myb Antisense Oligodeoxynucleotides in Colon Adenocarcinoma Cell Lines That Express c-myb," *Cancer Research* Jun. 1991, 51:2897-2901.
Meyer, "Overview of Enzymes of Drug Metabolism,"*Journal of Pharmacokinetics and Biopharmaceutics*, 1996, 24(5):449-459.
Mihalik et al., "Metabolomic Profiling of Fatty Acid and Amino Acid Metabolism in Youth With Obesity and Type 2 Diabetes," *Diabetes Care*, Mar. 2012, 35:605-611.
Mittelstrass et al., "Discovery of Sexual Dimorphisms in Metabolic and Genetic Biomarkers," *PLoSGenetics*, Aug. 2011, 7(8):1-12.
Muoio et al., "Molecular and metabolic mechanisms of insulin resistance and β-cell failure in type 2 diabetes," *Molecular Cell Biology*, Mar. 2008, 9:193-205.
Murray et al. "Glossary of terms for separations coupled to mass spectrometry," *Journal of Chromatography A*, 2010, 1217:3922-3928.
Navab et al. "Oral Synthetic Phospholipid (DMPC) Raises High-Density Lipoprotein Cholesterol Levels, Improves High-Density Lipoprotein Function, and Markedly Reduces Atherosclerosis in Apolipoprotein E-Null Mice," *Circulation*, 2003, 108:1735-1739.
Ostresh et al., "Generation and Use of Nonsupport-Bound Peptide and Peptidomimetic Combinatorial Libraries," *Methods in Enzymology*, 1996, 267:220-234.
Ozawa, "Strategic Proposals for Avoiding Toxic Interactions With Drugs for Clinical Use During Development and After Marketing of a New Drug—Proposals for Designing Non-Clinical and Clinical Studies—Is the Non-Clinical Study Useful?," *J Toxicol Sci*, Dec. 1996, 21(5):323-329.
Pabo et al., "Computer-Aided Model-Building Strategies for Protein Design," *Biochemistry*, 1986, 25:5987-5991.
Patsch et al., "Conditional Mutagenesis by Cell-Permeable Proteins: Potential, Limitations and Prospects," *Handbook of Experimental Pharmacology*, 2007, 178:203-232.
Postle, "Lipidomics," *Curr Opin Clin Nutr Metab Care*, 2012, 15:127-133.
Postle et al., "Dynamic lipidomics with stable isotope labelling," *Journal of Chromatography B*, 2009, 877:2716-2721.
Prossnitz et al., "Estrogen Signaling through the Transmembrane G Protein-Coupled Receptor GPR30," *Annual Review Physiology*, 2008, 70:165-190.
Qin et al., "Synthetic, Non-Natural Analogs of Ceramide Elevate Cellular Ceramide, Inducing Apoptotic Death to Prostate Cancer Cells and Eradicating Tumors in Mice," *Cancer Investigation*, 2010, 28:535-543.
Rathmann et al., "Incidence of Type 2 diabetes in the elderly German population and the effect of clinical and lifestyle risk factors: KORA S4/F4 cohort study," *DiabeticMedicine*, 2009, 26:1212-1219.
Römisch-Margl et al., "Procedure for tissue sample preparation and metabolite extraction for high-throughput targeted metabolomics," *Metabolomics*, 2012, 8:133-142.
Rose et al., "Three-Dimensional Structures of HIV-1 and SIV Protease Product Complexes," *Biochemistry*, 1996, 35:12933-12944.
Rutenber et al., "A New Class of HIV-1 Protease Inhibitor: The Crystallographic Structure, Inhibition and Chemical Synthesis of an Aminimide Peptide Isostere," *Bioorganic & Medicinal Chemistry*, 1996, 4(9):1545-1558.
Schier et al., "Efficient in vitro affinity maturation of phage antibodies using BIAcore guided selections," *Hum. Antibod. Hybridomas*, 1996, 7(3):97-105.
Schwarz et al., "Tools for Predicting the Risk of Type 2 Diabetes in Daily Practice," *Horm Metab Res*, 2009, 41:86-97.
Shevchenko et al., "Linking genome and proteome by mass spectrometry: Large-scale identification of yeast proteins from two dimensional gels," *Proc. Natl. Acad. Sci. USA*, Dec. 1996, 93:14440-14445.
Stumvoll et al., "Type 2 diabetes: principles of pathogenesis and therapy," *Lancet*, 2005, 365:1333-1346.
Suhre et al., "Metabolic Footprint of Diabetes: A multiplatform Metabolomics Study in an Epidemiological Setting," *PLoS ONE*, 2010, 5(11):1-11.
Tuomilehto et al., "Prevention of Type 2 Diabetes Mellitus by Changes in Lifestyle Among Subjects With Impaired Glucose Tolerance," *The New England Journal of Medicine*, May 2001, 344(18):1343-1350.
Turner et al., "Calpain-10: from genome search to function," *Diabetes Metab Res Rev*, 2005, 21:505-514.
Ulven et al., "Tissue-specific autoregulation of the LXRα gene facilitates induction of apoE in mouse adipose tissue," *Journal of Lipid Research*, 2004, 45:2052-2062.
van Meer et al., "Membrane lipids: where they are and how they behave," *Nature Reviews Molecular Cell Biology*, Feb. 2008, 9:112-124.
Violante et al., "Carnitine palmitoyltransferase 2: New insights on the substrate specificity and implications for acylcarnitine profiling," *Biochim. Biophys Acta*, Sep. 2010, 1802(9):728-732.
Wang et al., "Metabolite profiles and the risk of developing diabetes," *Nature Medicine*, Apr. 2011, 17(4):448-454.
Who, "Definition, Diagnosis and Classification of Diabetes Mellitus and its Complications," *Report of WHO Consultation*, World Health Organization, Department of Noncommunicable Disease Surveillance, Geneva, 1999, 65 pgs.
Wichmann et al., "KORA-gen—Resource for Population Genetics, Controls and a Broad Spectrum of Disease Phenotypes," *Gesundheitswesen*, 2005, 67(1):26-30.
Wilm et al., "Femtomole sequencing of proteins from polyacrylamide gels by nano-electrospray mass spectrometry," *Nature*, Feb. 1996, 379:466-469.
Wishart et al., "HMDB: the Human Metabolome Database," *Nucleic Acids Research*, 2007, 35:521-526.
Wishart et al., "HMDB: a knowledgebase for the human metabolome," *Nucleic Acids Research*, 2009, 37:603-610.
Wodak, "Computer-Aided Design in Protein Engineering," *Annals New York Academy of Sciences*, 1987, 501:1-13.
Ye, "Role of Insulin in the Pathogenesis of Free Fatty Acid-Induced Insulin Resistance in Skeletal Muscle," *Endocrine, Metabolic & Immune Disorders-Drug Targets*, 2007, 7(1):65-74.
Yu et al., "Human serum metabolic profiles are age dependent," *Aging Cell*, 2012, 11:960-967.
Zumbuehl, "Nonnatural Phospholipids: Probing Nature's Modular Platform," *Chimia*, 2009, 63(1/2):63-65.
Office Action issued in China for Application No. 201380051893.6 dated Jun. 23, 2016 (10 pages).
Office Action issued in Europe for Application No. 13748063.8-1405 dated Jul. 7, 2016 (7 pages).
European Search Report for Application No. 12180300 dated May 7, 2013 (18 pages).
Barber et al., "Plasma Lysophosphatidylcholine Levels are Reduced in Obesity and Type 2 Diabetes," *PLoS ONE*, vol. 7, No. 7, Jul. 25, 2012, 12 pages.
Castro-Perez et al., "Localization of Fatty Acyl and Double Bond Positions in Phosphatidylcholines Using a Dual Stage CID Fragmentation Coupled with Ion Mobility Mass Spectrometry," *J. Am. Soc. Mass Spectrum*, 2011 22:1552-1567.
Costa et al., "Quantitative Analysis of Plasma Acylcarnitines Using Gas Chromatography Chemical Ionization Mass Fragmentography," *Journal of Lipid Research*, vol. 38, 1997, pp. 173-182.
Huo et al., "Metabonomic Study of Biochemical Changes in Serum of Type 2 Diabetes Mellitus Patients After the Treatment of Metformin Hydrochloride," *Journal of Pharmaceutical and Biomedical Analysis*, 49 (2009) pp. 975-982.

(56) References Cited

OTHER PUBLICATIONS

Robert et al., "Glucose and Insulin Effects on de Novo Amino Acid Synthesis in Young Men: Studies with Stable Isotope Labeled Alanine, Gycline, Leucine, and Lysine," *Metabolism*, vol. 31, No. 2, 1982, pp. 1210-1218.

Wanninger et al., "Metformin Reduces Cellular Lysophosphatidylcholine and Thereby May Lower Apolipoprotein B Secretion in Primary Human Hepatocytes," *Biochimica et Biophysica Acta*, 2008, pp. 321-325.

* cited by examiner

BIOMARKERS FOR TYPE 2 DIABETES

This application is the §371 U.S. National Stage Entry of International Application No. PCT/EP2013/066914, filed 13 Aug. 2013, which claims priority to European Application No. 12180300.1 filed 13 Aug. 2012, each of which is incorporated by reference herein in its entirety.

The present invention relates to a method of identifying a predisposition for developing type 2 diabetes mellitus in a subject, said method comprising the step of assessing in a sample obtained from said subject the amount of one or more metabolite(s) selected from (a) a first group comprising the metabolites glycine, lysoPhosphatidylcholine acyl C18:2, lysoPhosphatidylcholine acyl C17:0, lysoPhosphatidylcholine acyl C18:0, lysoPhosphatidylcholine acyl C18:1, phosphatidylcholine acyl-alkyl C34:2, phosphatidylcholine acyl-alkyl C36:2, phosphatidylcholine acyl-alkyl C36:3 and isobaric metabolites having the same molecular mass as glycine, lysoPhosphatidylcholine acyl C18:2, lysoPhosphatidylcholine acyl C17:0, lysoPhosphatidylcholine acyl 018:0, lysoPhosphatidylcholine acyl 018:1, phosphatidylcholine acyl-alkyl 034:2, phosphatidylcholine acyl-alkyl C36:2 or phosphatidylcholine acyl-alkyl C36:3 but different chemical formula; and/or (b) a second group comprising the metabolite acetylcarnitine C2 and an isobaric metabolite having the same molecular weight as acetylcarnitine C2 but different chemical formula; wherein a decrease in the amount of a metabolite selected from said first group or an increase in the amount of a metabolite selected from said second group as compared to the amount of the corresponding metabolite(s) of a control is indicative of a predisposition to develop type 2 diabetes mellitus. Further, the invention relates to a method of identifying a compound capable of preventing type 2 diabetes mellitus and diseases associated therewith or serving as a lead compound for developing a compound capable of preventing type 2 diabetes mellitus and diseases associated therewith and a method of selecting a therapy to prevent type 2 diabetes mellitus. Also, the invention relates to a kit.

In this specification, a number of documents including Patent applications and manufacturer's manuals are cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

Type 2 diabetes mellitus (T2D) is a metabolic disease defined by increased blood glucose levels due to beta-cell dysfunction and insulin resistance, without evidence for specific causes such as autoimmune destruction of beta-cells (Stumvoll et al., *Lancet* 365, 1333-1346 (2005); Muoio et al., *Nat Rev Mol Cell Biol* 9, 193-205 (2008)). A state of pre-diabetes with only slightly higher blood glucose levels may precede the disease for years (McGarry et al., *Diabetes* 51, 7-18 (2002)) and increase also the risk for cardiovascular diseases (Schwarz et al., *Horm Metab Res* 41, 86-97 (2009)). The development of diabetes in pre-diabetic individuals can be prevented or delayed by dietary changes and increased physical activity (Tuomilehto et al., *N Engl J Med* 344, 1343-1350 (2001)). Risk prediction for T2D remains suboptimal even after the introduction of global risk assessment by various scores. The known risk factors for T2D include age, sex, anthropometric (obesity, blood lipids and blood pressure), metabolic (blood pressure, liver enzymes and uric acid), socioeconomic (leukocyte count, C-reactive protein and adiponectin) and life style (physical inactivity, dietary components, smoking and alcohol) variables (Lloyd et al., Int J Obes (Lond) 2012, 36(1):1-11; Gerich J E, Clinical cornerstone 2007, 8(3):53-68; Grundy S M, J Am Coll Cardiol 2012, 59(7):635-643; Aschner P, Expert review of cardiovascular therapy 2010, 8(3):407-412; Lechleitner M, Gerontology 2008, 54(5):253-259; Buijsse B et al., Epidemiol Rev 2011; 33:46-62). Pharmaceutical therapy (e.g. metformin, insulin injection) plays a significant role in the treatment of T2D. Life style intervention (e.g. dietary modification, exercise training and weight loss) may also improve glucose homeostasis. Improvement of risk prediction for T2D is crucial to the identification of high-risk individuals who could benefit from targeted preventive measures.

The technical problem underlying the present invention was to identify alternative and/or improved means and methods to identify subjects who are at risk to develop type 2 diabetes mellitus.

The solution to this technical problem is achieved by providing the embodiments characterized in the claims.

Accordingly, the present invention relates in a first embodiment to a method of identifying a predisposition for developing type 2 diabetes mellitus in a subject, said method comprising the step of assessing in a sample obtained from said subject the amount of one or more metabolite(s) selected from (a) a first group comprising the metabolites glycine, lysoPhosphatidylcholine acyl C18:2, lysoPhosphatidylcholine acyl C17:0, lysoPhosphatidylcholine acyl C18:0, lysoPhosphatidylcholine acyl C18:1, phosphatidylcholine acyl-alkyl C34:2, phosphatidylcholine acyl-alkyl C36:2, phosphatidylcholine acyl-alkyl C36:3 and isobaric metabolites having the same molecular mass as glycine, lysoPhosphatidylcholine acyl C18:2, lysoPhosphatidylcholine acyl C17:0, lysoPhosphatidylcholine acyl C18:0, lysoPhosphatidylcholine acyl C18:1, phosphatidylcholine acyl-alkyl C34:2, phosphatidylcholine acyl-alkyl C36:2 or phosphatidylcholine acyl-alkyl C36:3 but a different chemical formula; and/or (b) a second group comprising the metabolite acetylcarnitine C2 and an isobaric metabolite having the same molecular weight as acetylcarnitine C2 but a different chemical formula; wherein a decrease in the amount of a metabolite selected from said first group or an increase in the amount of a metabolite selected from said second group as compared to the amount of the corresponding metabolite(s) of a control is indicative of a predisposition to develop type 2 diabetes mellitus.

In an alternative embodiment, the method of the present invention relates to a method for producing diagnostically informative values of amounts of metabolites for identifying a predisposition for developing type 2 diabetes mellitus, the method comprising the steps recited above.

The term "predisposition for a disease" is established in the art and used herein analogously. Therefore, the term "predisposition for developing type 2 diabetes mellitus" describes the status of a patient at risk to develop type 2 diabetes mellitus (T2D). As used herein, the predisposition to develop T2D is based on environmental, genetic and/or epigenetic factors. Said predisposition to develop T2D may be diagnosed in a sample from a subject according to the method of the invention after said subject has been determined to exhibit an increase in blood glucose levels but can be diagnosed independently from and, in particular, prior to the latter determination. A "subject" in accordance with the method of the invention is preferably a human.

"Type 2 diabetes mellitus" as used herein relates to a condition characterized by the development of the symptoms of increased blood glucose levels believed to be the result of beta-cell dysfunction and insulin resistance. The criteria (as established by the World Health Organization) for the diagnosis of T2D include (a) fasting plasma glucose >=126 mg/dl and/or (b) two-hour post-glucose load plasma >=200 mg/dl during an oral glucose tolerance test with 75 g glucose and (c) $HbA_{1c}$>=6.5%.

T2D can be preceded by a state termed "pre-diabetes" which is characterized by elevated blood glucose levels alone and/or the incapability to efficiently clear glucose from the blood stream as mentioned herein above. The incapability to efficiently clear glucose from the blood stream is termed "impaired glucose tolerance" and is determined by the standardized oral glucose tolerance test which consists of a measurement of glucose plasma load two hours after challenge of the subject with 75 g glucose. A two-hour post glucose plasma load of ≥140 and <200 mg/dl qualifies a subject to have an impaired glucose tolerance (IGT). This condition may be accompanied by either normal (<110 mg/dl) or elevated fasting plasma glucose levels (<126 mg/dl). According to the state of the art definition of "pre-diabetes", a pre-diabetic subject may alternatively display only an elevated fasting blood glucose level and is then classified as having isolated-impaired fasting glucose (i-IFG): with a fasting glucose value of 110≤and <126 mg/dl, but two-hour post glucose plasma load of <140 mg/dl. However, and on the basis of the present invention with regard to the differing changes in the metabolite panels from NGT to i-IFG or to IGT (see FIG. 1), it becomes evident that a i-IFG and IGT are two different phenotypes. Thus, in accordance with the invention, the term "pre-diabetic" or "pre-diabetes" relates only to the presence of the status of impaired glucose tolerance (IGT). The following table provides an overview of the relation of i-IGF and IGT as referred to in accordance with the invention which are currently approved by the World Health Organization (World, H.O. Definition, diagnosis and classification of diabetes mellitus and its complications. Part 1: Diagnosis and classification of diabetes mellitus. *Report of a WHO consultation* (1999)).

|  | Fasting plasma glucose (mg/dl) |  | 2-h post-glucose load plasma values (mg/dl) |
|---|---|---|---|
| NGT | <110 | and | <140 |
| i-IFG | 110≤ and <126 | and | <140 |
| IGT | <126 | and | 140≤ and <200 |
| T2D | ≥126 | and/or | ≥200 |

The term "assessing the amount" as used herein in the context of metabolites refers to any method that can be employed to quantify the presence of one or more metabolite(s). The person skilled in the art is aware of experimental protocols that are suitable to determine the amount of one or more metabolite(s). For example, methods such as nuclear magnetic resonance (NMR) and/or mass spectrometry alone or in combination with, e.g., gas chromatography can be employed. The assessment of the "amount" of said one or more metabolite(s) is the decisive factor in the process of diagnosing a risk to develop T2D in accordance with the method of the invention. The amounts of metabolites generally and normally vary from subject to subject depending on age, sex and/or condition, inter alia, to a certain extent. As such, the amounts can be normalized. Several strategies for the normalisation of metabolite concentrations are known in the art, including, without being limiting, normalising against the concentration of an internal reference, which is determined in the same sample, normalisation against sample size, normalisation against total metabolite amount or normalisation against an artificially introduced molecule of known amount. In addition, normalisation may also be carried out by adjusting the obtained values by patient-specific factors such as e.g. age, BMI, hormone status, nutritional factors (e.g. fasting) or time (circadian rhythm). Normalisation can, for example, be achieved by dividing the measured values of the metabolite to be investigated by the measured values of a reference molecule or by subtracting the measured values of the reference molecule from the measured value of the metabolite of interest. Variations to be considered not normal, e.g., variations in metabolite amounts linked to a disease, have to be, preferably statistically, significant when compared to a suitable control population. In the present case, the amounts of the above recited metabolites were surprisingly found to be disturbed in pre-diabetic subjects with impaired glucose tolerance (IGT) as defined herein above.

Mass spectrometry and its use for determining the concentration of metabolites in a sample is well known in the art and has been described for example in Griffiths W J, Koal T, Wang Y, Kohl M, Enot D P, Deigner H P (2010) Targeted metabolomics for biomarker discovery. Angew Chem Int Ed Engl 49: 5426-5445, Koal T, Deigner H P (2010) Challenges in mass spectrometry based targeted metabolomics. Curr Mol Med 10: 216-226.

Mass spectrometry includes, for example, tandem mass spectrometry, matrix assisted laser desorption ionization (MALDI) time-of-flight (TOF) mass spectrometry, MALDI-TOF-TOF mass spectrometry, MALDI Quadrupole-time-of-flight (Q-TOF) mass spectrometry, electrospray ionization (ESI)-TOF mass spectrometry, ESI-Q-TOF, ESI-TOF-TOF, ESI-ion trap mass spectrometry, ESI Triple quadrupole mass spectrometry, ESI Fourier Transform mass spectrometry (FTMS), MALDI-FTMS, MALDI-Ion Trap-TOF, and ESI-Ion Trap TOF.

At its most basic level, mass spectrometry involves ionizing a molecule and then measuring the mass of the resulting ions. Since molecules ionize in a way that is well known, the molecular weight of the molecule can be accurately determined from the mass of the ions. In addition, by a comparison of data obtained from internal standards, a quantification of molecules of interest is possible, as detailed herein below.

Liquid chromatography mass spectrometry combines the physical separation capabilities of liquid chromatography (LC) or high-performance liquid chromatography (HPLC), with the mass analysis capabilities of mass spectrometry (MS) (Kushnir M M, Rockwood A L, Roberts W L, Yue B, Bergquist J, Meikle A W (2011) Liquid chromatography tandem mass spectrometry for analysis of steroids in clinical laboratories. Clin Biochem 44: 77-88; Murray K K (2010) Glossary of terms for separations coupled to mass spectrometry. J Chromatogr A 1217: 3922-3928). HPLC provides the advantage over L C that has a shorter analysis time and better resolution of analytes. This consequently increases selectivity, precision and accuracy of M S.

Tandem mass spectrometry involves first obtaining a mass spectrum of the ion of interest, then fragmenting that ion and obtaining a mass spectrum of the fragments. Tandem mass spectrometry thus provides both molecular weight information and a fragmentation pattern that can be used in combination along with the molecular weight information to identify the exact sequence of a peptide or protein, or small molecule (below 1500 Dalton) (see e.g. Hunt et al. (1986) PNAS USA 83:6233-6237; Shevchenko et al. (1996) PNAS USA 93:14440-14445; Figeys et al. (1996) Anal. Chem.

68:1822-1828 and Wilm et al. (1996) Nature 379:466-469); Kushnir M M, Rockwood A L, Roberts W L, Yue B, Bergquist J, Meikle A W: Liquid chromatography tandem mass spectrometry for analysis of steroids in clinical laboratories. Clin Biochem 2011, 44(1):77-88).

Preferably, if mass spectrometry is used, metabolite amounts are determined by reference to internal metabolite standards. The abundance of any molecular ion species typically carries information on concentration, but ion abundance is confounded by a number of features, including instrument response factors, ionisation efficiency of the molecule, stability of the molecular ion species and the presence of other molecules that could cause ion suppression of the analyte of interest. Thus, internal standards have been developed that can be used to generate appropriate calibration curves to convert abundance of ions into a quantitative measure of metabolite amounts. Non-limiting examples of internal standards include metabolite standards labelled with stable isotope-labelled versions of the metabolite to be quantified, which have a similar extraction recovery, ionization response and a similar chromatographic retention time; compound analogues of the metabolite to be quantified which are similar to the compound to be quantified but slightly different by parent mass; or chlorinated versions of the metabolite to be quantified, which commonly have a similar chromatographic retention time.

The internal standard is typically added at a known concentration into every sample, including the standards, at the beginning of the sample preparation, typically before the plasma preparation or solid phase extraction. It will be appreciated by the skilled person that the amount of the internal standard needs to be higher than the limit of quantitation but low enough to avoid a suppression of the ionization of the analyte. Based on the known concentration of the internal standard present in the sample, the measured values for the metabolite of interest can be quantified by interpolating the response ratio between the metabolite and the internal standard to a standard curve. These methods for determining metabolite concentrations by reference to internal metabolite standards are well known in the art and have been described, e.g. in Ciccimaro E, Blair I A (2010) Stable-isotope dilution LC-MS for quantitative biomarker analysis. Bioanalysis 2: 311-341; Koletzko B, Demmelmair H, Hartl W, Kindermann A, Koletzko S, Sauerwald T, Szitanyi P (1998) The use of stable isotope techniques for nutritional and metabolic research in paediatrics. Early Hum Dev 53 Suppl: S77-97; Postle A D, Hunt A N (2009) Dynamic lipidomics with stable isotope labelling. Journal of chromatography B, Analytical technologies in the biomedical and life sciences 877: 2716-2721).

Preferably, the internal metabolite standards are stable isotope-labelled standards. As is known, stable in the context of isotopes means that the isotopes are not radioactive, i.e. they do not decay spontaneously. Metabolite standards labelled with (a) stable isotope(s) are stable isotope-labelled versions of the metabolite to be quantified and are well known in the art. Typically, the isotopes employed are stable isotopes of carbon, nitrogen or hydrogen, such as e.g. $^{12}C$ and $^{13}C$, $^{14}N$ and $^{15}N$ and $^{2}H$ (Deuterium). Such stable isotope-labelled metabolite standards have been described e.g. in Lee et al. Clinical Biochemistry 43 (2010): 1269-1277.

The term "sample" as used herein refers to a biological sample, such as, for example, cells, tissues (from any organ), or fluids (including serum, plasma, whole blood), which has been isolated or obtained from an individual or from cell culture constituents of a cell culture comprising a subject's cells. Any tissue or liquid sample obtained from a patient and/or subject that comprises cells can be used for the assessment of the amount of the one or more metabolite(s) according to the method of the invention. Examples of cell types are hepatocytes, cardiomyocytes, adipocytes, myocytes, epithelial cells (of kidney, lung or cardiovascular origin) and fibroblasts, and cells derived from these (e.g. immortalised cell lines or induced pluripotent stem cell lines). It is well known in the art that proteins (as are metabolites) of individuals can easily be obtained from blood samples (from whole blood, serum or plasma). Thus, a preferred sample to assess metabolite amounts in accordance with the method of the invention is blood, serum and/or plasma. Methods for preparing the sample for protein extraction, if desired, are well known in the art, and can be carried out using commercially available kits such as, for example, the AbsoluteIDQ™ p180 and p150 kits from BIOCRATES Life Sciences AG (Innsbruck, Austria).

For the assessment of the amount of one or more metabolite(s) in a sample, the sample may need to be manipulated depending on the type of sample and the method chosen for assessment. For example, in the case of blood and when using the AbsoluteIDQ™ p150 kit (BIOCRATES Life Sciences AG, Innsbruck, Austria). For example, blood can be drawn into suitable containers (e.g., tubes such as S-Monovette® serum tubes (SARSTEDT AG & Co., Nümbrecht, Germany)) followed by one or more gentle inversions of the containers, and letting the samples rest for 30 minutes at room temperature to obtain complete coagulation. For serum collection, centrifugation of blood, e.g. at 2750 g and 15° C. for 10 minutes, can be performed. Serum can then be separated and, if desired, filled into containers, e.g., synthetic straws, for storage, such as in liquid nitrogen (−196° C.), until the execution of metabolic analyses.

The term "metabolite" is used in line with its well-known meaning in the art. Briefly, intermediate and end products of metabolism are termed metabolites (also referred to sometimes as small molecules or analytes with a molecular mass of less than 1500 Dalton). Metabolites are classified into primary metabolites that are directly involved in normal growth, development and reproduction. Secondary metabolites are not directly involved in the latter processes, but may have important ecological functions (e.g., antibiotics, pigments). Exemplary biological functions of metabolites include serving as intermediate or end-point products in biosynthesis pathways or as cellular signaling molecules (e.g., in energy homeostasis, regulation of lipid and sugar transport (e.g., CPT, GLUT4), and non-nuclear receptors such as the GPR-family, nuclear receptors such as PPAR, LXR or FXR (Violante et al., Biochim Biophys Acta 2010, 1802(9):728-732; Turner et al., Diabetes Metab Res Rev 2005, 21(6):505-514; Ulven et al., J Lipid Res 2004, 45(11): 2052-2062; van Meer et al., Nat Rev Mol Cell Biol 2008, 9(2)112-124; Jones et al., Proc Natl Acad Sci USA 2005, 102(17):6207-6212; Prossnitz et al., Annu Rev Physiol 2008, 70:165-190; Ye J, Endocr Metab Immune Disord Drug Targets 2007, 7(1):65-74; Chiang J Y, Endocr Rev 2002, 23(4):443-463; Makishima M, J Pharmacol Sci 2005, 97(2): 177-183.). It is thus becoming a key tool in functional annotation of genes and in the comprehensive understanding of the cellular response to biological conditions.

The characteristics of metabolites referred to herein are contained in the below table. As evident from the below table, for the metabolites as used in accordance with the method of the invention, identification numbers are provided from the human metabolome database HMDB (Wishart et al., 2007, Wishart et al., 2009) version 2.5.

| Metabolites | Mass (g/mol) | Formula | HMDB IDs | HMDB IDs (alternative) |
|---|---|---|---|---|
| Glycine (Gly) | 75.07 | $C_2H_5NO_2$ | HMDB00123 | |
| lysoPhosphatidylcholine acyl C18:2 (LPC (18:2)) | 519.65 | $C_{26}H_{50}NO_7P$ | HMDB10386 | |
| Acetylcarnitine C2 | 203.23 | $C_9H_{17}NO_4$ | HMDB00201 | |
| lysoPhosphatidylcholine acyl C17:0 (LPC (17:0)) | 509.65 | $C_{25}H_{52}NO_7P$ | HMDB12108 | |
| lysoPhosphatidylcholine acyl C18:0 (LPC (18:0)) | 523.68 | $C_{26}H_{54}NO_7P$ | HMDB10384 | |
| lysoPhosphatidylcholine acyl C18:1 (LPC (18:1)) | 521.67 | $C_{26}H_{52}NO_7P$ | HMDB10385 | |
| phosphatidylcholine acyl-alkyl C34:2 (PC ae C34:2) | 744.07 | $C_{42}H_{82}NO_7P$ | HMDB11151 (16:0/18:2) | |
| phosphatidylcholine acyl-alkyl C36:2 (PC ae C36:2) | 772.13 | $C_{44}H_{86}NO_7P$ | HMDB13418 (18:0/18:2) | HMDB13428 (18:1/18:1) |
| phosphatidycholine acyl-alkyl C36:3 (PC ae C36:3) | 770.11 | $C_{44}H_{84}NO_7P$ | HMDB13425 (18:1/18:2) | HMDB13429 (18:1/18:2) |

The metabolites referred to herein are abbreviated using standard abbreviations well known in the art. For example, "PC" abbreviates phosphatidylcholines, The term "Cx:y" is used to describe the total number of carbons (x) and the number of double bonds (y) of all chains. Glycerophospholipids are distinguished with respect to the presence of ester (a) and ether (e) bonds in the glycerol moiety, where two letters (aa=diacyl, ae=acyl-alkyl) denote that the two glycerol positions are each bound to a fatty acid residue, while a single letter (a=acyl or e=alkyl) indicates the presence of a single fatty acid residue. For example "PCae C34:1" denotes a glycerophosphatidylcholine with an acyl (a) and an ether (e) side chain, with 34 carbon atoms in both side chains and a single double bond in one of them.

The term "isobaric" is well-known in the art and in relation to metabolites as used herein refers to metabolites having the same molecular mass as a given metabolite identified herein as being a risk factor for the development of T2D. Albeit having the same molecular mass (as identified by method described herein) in comparison to a metabolite identified herein as being a risk factor for the development of T2D, an isobaric metabolite has a different chemical formula.

In accordance with the method of the present invention, a hard or soft copy comprising the values of amounts of metabolites determined is optionally prepared. Non-limiting examples of hard copies include print-outs, hand-written information as well as photographs or the data as originally obtained, for example from a mass spectrometer. Non-limiting examples of soft copies include any form of computer files such as the originally obtained data output from the machine performing the measurements (e.g. a mass spectrometer) or from the respective analysis programme or e.g. word or other text software documents containing the values, as well as e.g. screen shots.

It will be appreciated that the values comprised in said hard or soft copy can e.g. be calculated values, for example in the form of numerical values derived from the measurements as well as the original data as obtained. In accordance with the present invention, the option of preparing a hard or soft copy comprising the values of amounts of metabolites determined can be applied to either the method of identifying a predisposition for developing type 2 diabetes mellitus of the present invention, or to the method for producing diagnostically informative values of amounts of metabolites for identifying a predisposition for developing type 2 diabetes mellitus of the invention.

In order to identify a predisposition for developing T2D, the amount of said one or more metabolite(s) described herein in a sample of a subject suspected to be predispositioned to develop T2D are compared to the amount of the corresponding metabolite(s) of a control. A control is selected from i) a group of subjects (termed herein also "control group") negative for T2D, exhibiting no impaired glucose tolerance (IGT) and, optionally, exhibiting no isolated impaired fasting glucose (i-IFG), i.e. the control group has a fasting plasma glucose <110 mg/dl and two-hour post-glucose plasma load <140 mg/dl during an oral glucose tolerance test with 75 g glucose, and, optionally displays a $HbA_{1c}$<5.7% and is representative (with regard to, e.g., same distribution of age, race, sex, health status) for the investigated population, and ii) database entries. Said group of subjects preferably consist of a suitably large number of subjects, so as to yield representative results. Preferably, the amounts in samples of at least (for each value) 4, 6, 8, 10, 20, 50, 100, 200 or more preferred at least 400, even more preferred at least (for each value) 500, 600, 700, 800 and most preferred 1000 and more control subjects are determined. This might be advantageous, because some individuals of the control group may potentially display elevated amounts of said one or more metabolite(s), i.e. they are at risk to develop T2D, but could, conceivably, not be determined to be at risk prior to the invention on the basis of said risk factors. It is understood herein, that in accordance with the findings of the invention said control group according to i) does not comprise individuals with metabolite amounts indicative for the person to be at risk of developing T2D. Nevertheless, a control group according to i) may be normalized to exclude subjects which are at risk to develop T2D, for example, on the basis of biomarkers other than those according to the invention, so as to (further) refine the initial control data. Conceivably, increasing the number of subjects in the control group will result in a more accurate and representative result to be used as normal amount of a given metabolite in a control. Also preferred is that the metabolite amounts are determined more than once or that several samples of a subject of the control group are assessed. The data of said several samples, said several tests and/or of said subjects of the control group is pooled to calculate the mean or median and, optionally, the variance for each subject in the case of several samples or tests, and/or the variance for the group of control subjects. These values may, e.g., be deposited into a database as a standardized value for each of said one or more metabolite(s) and if required retrieved from a database, hence making the need to also experimentally assess the metabolite amounts in a control sample every time the amount in a patient sample is assessed dispensable. Accordingly, a control may also be a database entry, i.e. the control according to item ii) above. Moreover, by using the variance of the metabolite amount of the control sample, the statistical significance of deviations from the mean of controls in the sample to be assessed may be determined. Finally, and where deemed appropriate, age- or sex-specific or otherwise biased controls may be used.

In accordance with the present invention, for the first time an association of metabolite amounts, i.e. those mentioned above, and development of T2D is demonstrated. In brief, a comprehensive screening and quantification of metabolites was performed in the population-based KORA baseline and follow-up cohorts S4/F4 (Rathmann et al., *Diabet Med* 26, 1212-1219 (2009)). This study revealed metabolic deviations in IGT individuals that are distinct from common T2D risk indicators (Rathmann et al., *Diabet Med* 26, 1212-1219 (2009); Lyssenko et al., *N Engl J Med* 359, 2220-2232 (2008)), including, e.g., fasting glucose (FG), glycosylated hemoglobin (HbA1c) (ADA. Executive summary: Standards of medical care in diabetes—2010. *Diabetes Care* 33 Suppl 1, S4-10 (2010).) and fasting insulin (see FIGS. 2 and 3). These deviations could be replicated in the EPIC-Potsdam cohort (Boeing et al., *Ann Nutr Metab* 43, 195-204 (1999)). As such, and in accordance with the method of the invention, a subject can be identified to be at risk to develop T2D on the basis of metabolites and, importantly, prior to an impaired glucose tolerance and independent from the above recited commonly known risk factors for the development of T2D. Conceivably, and as subjects exhibiting impaired glucose tolerance can delay or prevent the development of T2D, the method of the invention allows early medical intervention including, e.g., change of lifestyle and/or treatment with pharmaceuticals. The method of the invention opens up a completely new therapeutic time frame for prevention of T2D allowing medical intervention before critical events like, e.g., impaired glucose tolerance can affect a subject's health. Corresponding intervention will help maintain health in subjects at risk for developing T2D. Assessment of the amounts of the above recited one or more metabolite(s) will identify subjects who will benefit from preventive medical intervention, thus saving the health of the individual possibly by reversing and/or delaying the development of the T2D disease, and reduce costs for the health-care system.

In a further embodiment the invention relates to a method of identifying a compound capable of preventing type 2 diabetes mellitus and diseases associated therewith or serving as a lead compound for developing a compound capable of preventing type 2 diabetes mellitus and diseases associated therewith, the method comprising the steps of: (a) assessing the amount of one or more metabolite(s) selected from i. a first group comprising the metabolites glycine, lysoPhosphatidylcholine acyl C18:2, lysoPhosphatidylcholine acyl C17:0, lysoPhosphatidylcholine acyl C18:0, lysoPhosphatidylcholine acyl C18:1, phosphatidylcholine acyl-alkyl C34:2, phosphatidylcholine acyl-alkyl C36:2 and phosphatidylcholine acyl-alkyl C36:3 and isobaric metabolites having the same molecular mass as glycine, lysoPhosphatidylcholine acyl C18:2, lysoPhosphatidylcholine acyl C17:0, lysoPhosphatidylcholine acyl C18:0, lysoPhosphatidylcholine acyl C18:1, phosphatidylcholine acyl-alkyl C34:2, phosphatidylcholine acyl-alkyl C36:2 or phosphatidylcholine acyl-alkyl C36:3 but a different chemical formula; and/or ii. a second group comprising the metabolite acetylcarnitine C2 and an isobaric metabolite having the same molecular weight as acetylcarnitine C2 but a different chemical formula, in a cell contacted with a test compound or in a sample obtained from a subject and contacted with said test compound; and (b) assessing the amount of said one or more metabolite(s) in a cell or a sample obtained from a subject, wherein said cell or sample was i. not contacted with said test compound; ii. contacted with a compound known to not affect the amount of said one or more metabolite(s) of step (a), wherein an increase in the amount of a metabolite selected from said first group or a decrease in the amount of a metabolite selected from said second group in step (a) as compared to step (b) i. or (b) ii. is indicative of said test compound being capable of preventing type 2 diabetes mellitus and diseases associated therewith or serving as a lead compound for developing a compound capable of preventing type 2 diabetes mellitus and diseases associated therewith; or iii. contacted with a compound known to increase the amount of said at least one metabolite selected from said first group and/or to decrease the amount of said at least one metabolite selected from said second group of step (a), wherein an essentially equal amount or an increase of the amount of said at least one metabolite selected from said first group and/or a decrease in the amount of said at least one metabolite selected from said second group of step (a) as compared to step (b) iii. is indicative of the compound being capable of preventing type 2 diabetes mellitus and diseases associated therewith or serving as a lead compound for developing a compound capable of preventing type 2 diabetes mellitus and diseases associated therewith.

Methods for the assessment of metabolite amounts are well-known in the art and some are exemplarily described herein. The amount of the one or more metabolite(s) is to be assessed in a cell or in a sample obtained from a subject contacted with the test compound. Said cell may be part of a cell culture colony derived from an established cell line. The cells could be hepatocytes, cardiomyocytes, adipocytes, myocytes, epithelial cells (of kidney, lung or cardiovascular origin) and fibroblasts, and cells derived from these (e.g. immortalised cell lines or induced pluripotent stem cell lines). Also, the cell may be part of a primary cell culture established from a sample of a subject contacted with the test compound. Suitable samples obtained or obtainable from subjects for the assessment of metabolite amounts are described herein elsewhere and may also be processed without prior steps, such as establishing a primary cell culture, in order to assess metabolite amounts.

The term "compound" as used herein relates to a substance that may be solid, semisolid, semifluid, fluid or gaseous. Said compound may, however, also be comprised in a mixture, extract or composition.

The compound that is identified according to the method of the invention to be capable of preventing T2D and diseases associated therewith or capable of serving as a lead compound for developing a compound capable of preventing T2D and diseases associated therewith increases the amount of said one or more metabolite(s) selected from said first group of metabolites and/or decreases the amount of said one or more metabolite(s) selected from said second group of metabolites, which may, for example, be based on its inhibitory, promoting, agonistic or antagonistic activity in a direct or indirect interaction with the metabolite itself, with genes involved in the metabolic pathway of a given metabolite or with any intermediate or final gene product(s). Said compound(s) may be chemically synthesized or produced via microbial fermentation but can also be comprised in, for example, samples, e.g., cell extracts from, e.g., plants, animals or microorganisms.

Furthermore, said compound to be identified by the method of the invention may be known in the art but hitherto not known to be useful as a compound capable of preventing T2D. Diseases associated with T2D are diseases whose onset and/or persistence are causally related to the development and/or presence of T2D or have been shown to develop and persist simultaneously with T2D (such as e.g., cardiovascular diseases (e.g., stroke, heart attack), diabetic retinopathy and neuropathy, or kidney failure). Also envisaged is that diseases associated with T2D are diseases that the subject is afflicted with prior to developing T2D and that are modulated such as, e.g., exacerbated or shifted to a chronic status from an acute status upon development and/or presence of T2D.

The term "contacting a cell" with a compound in accordance with the method of the invention relates to the process of exposing the cell to a compound to be tested and allowing interaction of said compound with the cell. Depending on the potential mode of action of the compound to be tested the interaction may take place extracellularly and/or intracellularly resulting in the increase of the amount of said one or more metabolite(s) selected from said first group of metabolites and/or in the decrease of the amount of said one or more metabolite(s) selected from said second group of metabolites—provided the compound is capable thereof. For example, a compound may bind to the cell surface and trigger a signal cascade resulting in an increase and/or decrease of said metabolite amounts. However, preferably the compound is exposed to the cell under conditions allowing both extracellular interaction and the uptake into the cell, in particular the cytoplasma or nucleus, to exert its potential activity on regulatory events in the metabolic pathway of a given metabolite. The person skilled in the art is aware of conditions generally suitable for uptake of compounds such as, e.g., proteins or nucleic acid molecules, into cells and methods to enhance said uptake as regards rate and amount wherein said enhancement may include artificially modifying, e.g, proteins (see, for example, Patsch et Edenhofer, (2007), Handb. Exp. Pharmacol., 178, 203-232) or nucleic acids. Furthermore, he is also aware of cell lines naturally exhibiting the capacity of increased uptake capabilities relative to other cells. Such cells are, for example, cells like mucosal cells or intestinal cells. A number of mechanisms exist for the passage of various compounds across the plasma membrane, including passive diffusion, facilitated diffusion, and active transport systems. Passive diffusion of proteins through the bilayer lipid structure of the plasma membrane is a function of the size, lipid solubility, and charge of the protein molecule. A further uptake mechanism is endocytosis. Endocytosis is a process whereby cells absorb material from the outside by engulfing it with their cell membrane. Endocytosis works with macromolecules or particulate matter beyond a certain size threshold and also with fluids (pinocytosis). Correspondingly, the test compound should be contacted with the subject in a way that allows for the interaction of the test compound with cells that are part of the sample to be subsequently obtained from said subject and assessed in accordance with the method of the invention. For example, if blood is intended to be obtained as a sample from the subject, intravenous administration of the test compound—if necessary as part of a therapeutically acceptable composition—will be suitable to allow for an interaction of cells of the sample with the test compound. Accordingly, said test compound may be, e.g., added to the culture medium or injected into a cell or administered to an individual prior to the assessment of the metabolite amounts in step (a). Moreover, the compound to be identified can be contained in libraries of small molecules, such as organic or inorganic small molecules which may be commercially available. In addition, libraries comprising antibodies or functional fragments or derivatives thereof (i.e. fragments or derivatives maintaining the binding specificity of the original antibody) may be used as a starting point in the identifying process. Suitable libraries are commercially available, for example from ChemBridge Corp., San Diego, USA. Also, libraries of aptamers such as peptide aptamers might be employed. The skilled person is of course free to use any other starting point of desired compounds for use in the method of the invention.

If a composition containing (a) compound(s) is identified to be capable of preventing T2D and diseases associated therewith or serving as a lead compound for developing a compound capable of preventing T2D or diseases associated therewith in the method of the invention, then it is either possible to isolate the active compound(s) from the original composition identified as containing the compound(s) in question or one can further subdivide the original composition, for example, if it consists of a plurality of different test compounds, so as to reduce the number of different substances per sample and repeat the method with the subdivisions of the original composition. It can then be determined whether said subdivided composition or resulting compound displays the desired properties, for example, by the methods described herein or in the literature ("Cells: A laboratory manual", v. 1-3, edited by Spector et al., Cold Spring Harbour Laboratory Press (1997); ISBN 10: 0879695218). Depending on the complexity of the compositions, the steps described above can be performed several times, preferably until the composition identified according to the method of the invention only comprises a limited number of or only one substance(s). Preferably said composition comprises substances of similar chemical and/or physical properties. The method of the present invention can be easily performed and the experimental setup without further ado designed by the person skilled in the art, for example, in accordance with other cell based screening assays described in the prior art. Such adaptation of the method of the invention is well within the skill of the person skilled in the art and can be performed without undue experimentation.

Compounds which can be tested in accordance with the present invention include peptides, proteins, nucleic acids, antibodies, small organic compounds, ligands, peptidomimetics, PNAs and the like. Depending on whether the amount of the first or second of metabolites is tested for, said compounds may act as agonists or antagonists. Said compounds can also be functional derivatives or analogues of known drugs. Methods for the preparation of chemical derivatives and analogues are well known to those skilled in the art and are described in, for example, Beilstein, Handbook of Organic Chemistry, Springer edition New York Inc., 175 Fifth Avenue, New York, N.Y. 10010 U.S.A. and Organic Synthesis, Wiley, New York, USA. Also, peptide mimetics and/or computer-aided design of appropriate drug derivatives and analogues can be used.

Appropriate computer programs can be used for the identification of interactive sites of a compound putatively capable of preventing T2D and diseases associated therewith by computer assisted searches for complementary structural motifs (Fassina, Immunomethods 5 (1994), 114-120). Further appropriate computer systems for the computer aided design of protein and peptides are described in the prior art, for example, in Berry, Biochem. Soc. Trans. 22 (1994), 1033-1036; Wodak, Ann. N. Y. Acad. Sci. 501 (1987), 1-13; Pabo, Biochemistry 25 (1986), 5987-5991. The results obtained from the above-described computer analysis can be used in combination with the method of the invention for, e.g., optimizing known inhibitors, analogs, antagonists or agonists. Appropriate peptidomimetics can also be identified by the synthesis of peptidomimetic combinatorial libraries through successive chemical modification and testing the resulting compounds, e.g., according to the methods described or referred to herein. Methods for the generation and use of peptidomimetic combinatorial libraries are described in the prior art, for example in Ostresh, Methods in Enzymology 267 (1996), 220-234 and Dorner, Bioorg. Med. Chem. 4 (1996), 709-715. Furthermore, the three-dimensional and/or crystallographic structure of said compounds can be used for the design of peptidomimetic drugs (Rose, Biochemistry 35 (1996), 12933-12944; Rutenber, Bioorg. Med. Chem. 4 (1996), 1545-1558). It is well known how to obtain compounds to be tested in the method of the invention, e.g. by chemical or biochemical standard techniques. Thus, also comprised by the method of the invention are means of making or producing said compounds. In summary, the present invention provides a method for identifying compounds which can be used for the prevention of T2D and diseases associated therewith.

Also, the method of the invention may be useful in identifying lead compounds. The term "lead compound" in accordance with the present invention refers to a compound discovered by the method of the invention which will be e.g. further optimized, in particular to be pharmaceutically more acceptable. The identified lead compounds may be optimized to arrive at a compound which may be, for example, used in a pharmaceutical composition for preventing T2D. Methods for the optimization of the pharmacological properties of compounds identified in screens, the lead compounds, are known in the art and comprise a method of modifying a compound identified as a lead compound to achieve: (i) modified site of action, spectrum of activity, organ specificity, and/or (ii) improved potency, and/or (iii) decreased toxicity (improved therapeutic index), and/or (iv) decreased side effects, and/or (v) modified onset of therapeutic action, duration of effect, and/or (vi) modified pharmacokinetic parameters (resorption, distribution, metabolism and excretion), and/or (vii) modified physico-chemical parameters (solubility, hygroscopicity, color, taste, odor, stability, state), and/or (viii) improved general specificity, organ/tissue specificity, and/or (ix) optimized application form and route by (i) esterification of carboxyl groups, or (ii) esterification of hydroxyl groups with carboxylic acids, or (iii) esterification of hydroxyl groups to, e.g. phosphates, pyrophosphates or sulfates or hemi-succinates, or (iv) formation of pharmaceutically acceptable salts, or (v) formation of pharmaceutically acceptable complexes, or (vi) synthesis of pharmacologically active polymers, or (vii) introduction of hydrophilic moieties, or (viii) introduction/exchange of substituents on aromates or side chains, change of substituent pattern, or (ix) modification by introduction of isosteric or bioisosteric moieties, or (x) synthesis of homologous compounds, or (xi) introduction of branched side chains, or (xii) conversion of alkyl substituents to cyclic analogues, or (xiii) derivatisation of hydroxyl group to ketales, acetales, or (xiv) N-acetylation to amides, phenylcarbamates, or (xv) synthesis of Mannich bases, imines, or (xvi) transformation of ketones or aldehydes to Schiffs bases, oximes, acetales, ketales, enolesters, oxazolidines, thiazolidines or combinations thereof.

The various steps recited above are generally known in the art. They include or rely on quantitative structure-activity relationship (QSAR) analyses (Kubinyi (1992) "Hausch-Analysis and Related Approaches", VCH Verlag, Weinheim), combinatorial biochemistry, classical chemistry and others (see, for example, Holzgrabe and Bechtold (2000) Deutsche Apotheker Zeitung 140(8), 813).

The therapeutically useful compounds identified according to the method of the invention can be formulated and administered to a patient by methods well known in the art. Drugs or pro-drugs after their in vivo administration are metabolized in order to be eliminated either by excretion or by metabolism to one or more active or inactive metabolites (Meyer, J. Pharmacokinet. Biopharm. 24 (1996), 449-459). More specifically, a "prodrug" is a compound that is generally not biologically and/or pharmacologically active. After administration, the prodrug is activated, typically in vivo by enzymatic or hydrolytic cleavage and converted to a biologically and/or pharmacologically compound which has the intended medical effect. Prodrugs are typically formed by chemical modification of biologically and/or pharmacologically compounds. Conventional procedures for the selection and preparation of suitable prodrugs are described, for example, in Design of Prodrugs, ed. H. Bundgaard, Elsevier, 1985. Thus, rather than using the actual compound identified in accordance with the method of the present invention a corresponding formulation as a pro-drug can be used which is converted into its active in the patient. Precautionary measures that may be taken for the application of pro-drugs and drugs are described in the literature; see, for review, Ozama, J. Toxicol. Sci. 21 (1996), 323-329.

Preferably, said method is effected in high-throughput format. High-throughput assays, independently of being biochemical, cellular or other assays, generally may be performed in wells of microtiter plates, wherein each plate may contain 96, 384 or 1536 wells. Handling of the plates, including incubation at temperatures other than ambient temperature, and bringing into contact of test compounds with the assay mixture is preferably effected by one or more computer-controlled robotic systems including pipetting devices. In case large libraries of test compounds are to be screened and/or screening is to be effected within short time, mixtures of, for example 10, 20, 30, 40, 50 or 100 test compounds may be added to each well. In case a well exhibits biological activity, said mixture of test compounds may be de-convoluted to identify the one or more test compounds in said mixture giving rise to said activity.

The above definitions apply mutatis mutandis to the methods described in the following.

This method of the invention is based upon the presumption that the increase of the amount of said one or more metabolite(s) selected from said first group of metabolites and/or the decrease of the amount of said one or more metabolite(s) selected from said second group of metabolites is suitable to prevent the development of T2D and diseases associated therewith in a subject. As described herein above, said metabolite(s) are associated with the risk of developing T2D and their amounts are either decreased or increased, respectively, in subjects at risk for developing T2D The increase and/or decrease in metabolite amount(s) is determined vis-à-vis the corresponding metabolite amount(s) of a control sample or cell in step (b). For step (b) serving as control, it is self-evident that the control samples of step (b) i), ii) or iii) are not to be contacted with the test compound referred to in step (a). Said control sample or cell may be a sample or cell that has not been contacted with the compound to be tested. Additionally or alternatively, the metabolite amounts of the sample or cell may be compared to the corresponding metabolite amount(s) of a sample or cell that has been contacted with a compound known to not affect the amounts of the metabolite(s). It is also envisaged that in addition to the comparison of the metabolite amounts of the cells or the sample of step (a) against the one or both latter negative controls a comparison against a sample or cell contacted with a compound known to increase the amount of said one or more metabolite(s) of said first group and/or to decrease the amount of said one or more metabolite(s) of said second group is effected. A corresponding method provides a qualitative assessment of the compound to be tested. It is alternatively possible to exclusively compare metabolite amount(s) of the cell or sample of step (a) against the corresponding metabolite amount(s) of a cell or sample that has been contacted with a compound known to increase the amount of said at least one metabolite selected from said first group and/or to decrease the amount of said at least one metabolite selected from said second group, if it is desired to screen for compounds that have a similar or superior effect on the metabolite amount(s) as the latter control. A corresponding experimental setup would hence allow identifying compounds that are similar or superior to existing compounds that are capable of increasing the amount of said at least one metabolite selected from said first group and/or decreasing the amount of said at least one metabolite selected from said second group. In other words, corresponding compounds may be capable of effecting an essentially equal or higher increase of the amounts of the one or more metabolite(s) of said first group and/or an essentially equal or higher decrease of the amounts of the one or more metabolite(s) of said first group as compared to said compound known to increase the amount of said at least one metabolite selected from said first group and/or to decrease the amount of said at least one metabolite selected from said second group. The term "essentially equal" refers to a metabolite amount(s) that are about 90% to about 110%, such as about (for each value) 91% to about (for each value) 109%, 92% to 108%, 93% to 107%, 94% to 106%, 95% to 105%, 96% to 104%, 97% to 103%, 98% to 102%, 99% to 101% or 100% as high as the corresponding metabolite amount(s) of the cell or sample that has been contacted with the compound known to increase the amount of said at least one metabolite selected from said first group and/or to decrease the amount of said at least one metabolite selected from said second group. Also, and when not essentially equal, the metabolite amount(s) could be greater than 110% such as, e.g., at least 111%, 112%, 113%, 114%, 115%, or preferably at least 116% or 117%, more preferred at least 120% or 130% and most preferred at least 200% or more as high as the corresponding metabolite amount(s) of the cell or sample that has been contacted with said compound known to increase the amount of said at least one metabolite selected from said first group or as low as the corresponding metabolite amount(s) of the cell or sample that has been contacted with said compound known to decrease the amount of said at least one metabolite selected from said second group. Depending on the potency of the compound known to increase the amount of said at least one metabolite selected from said first group and/or to decrease the amount of said at least one metabolite selected from said second group, it may not be possible to further to increase the amount of said at least one metabolite selected from said first group and/or to decrease the amount of said at least one metabolite selected from said second group. Accordingly, suitable compounds to be identified by the method of the invention may in comparison only achieve a fraction of the increase of the amount of said at least one metabolite selected from said first group and/or the decrease of the amount of said at least one metabolite selected from said second group of the above defined positive control. Hence, compounds that only result in an increase of the amount of said at least one metabolite selected from said first group and/or a decrease of the amount of said at least one metabolite selected from said second group of at least 5%, such as at least 10%, 20%, 30%, 40%, 50%, or preferably at least 60% or 70% and most preferred at least 80% or at least 89% as compared to the metabolite amount(s) of the cell or sample that has been contacted with the compound known to increase the amount of said at least one metabolite selected from said first group and/or to decrease the amount of said at least one metabolite selected from said second group can also be identified in accordance with the method of the invention. Accordingly, the identification of compounds that are capable of adjusting the amount of the risk metabolite(s) as described herein towards the amount of the corresponding metabolite(s) in a person not at risk for T2D, preferably selectively and in a dose-dependent fashion, provides the means for a drug-based therapeutic intervention.

The above applies mutatis mutandis to other embodiments recited herein.

In a preferred embodiment of the method of identifying a compound capable of preventing type 2 diabetes mellitus and diseases associated therewith or serving as a lead compound for developing a compound capable of preventing type 2 diabetes mellitus and diseases associated therewith, the method further comprises synthesizing said compound being capable of preventing type 2 diabetes mellitus and diseases associated therewith or serving as a lead compound for developing a compound capable of preventing type 2 diabetes and diseases associated therewith.

As outlined above, it is well-known in the art how to obtain, produce and modulate the test compounds, e.g. by chemical or biochemical standard techniques. Thus, having identified a compound that is capable of preventing T2D and diseases associated therewith or serving as a lead compound for developing a compound capable of preventing T2D and diseases associated therewith, the skilled person is in the position to synthesize said identified compound in desired amounts by employing said chemical or biochemical standard techniques. For example, and relating to small molecules, antisense nucleic acid molecules, siRNAs, shRNAs, miRNAs, ribozymes, peptide aptamers, nucleic acid based aptamers and antibodies as test and/or identified compounds, methods how to obtain, produce and modulate the latter are described herein below.

In a further preferred embodiment of the methods of the invention, the amount of said one or more metabolite(s) selected from said first group being decreased and/or from said second group being increased is detectable or detected in a subject prior to said subject exhibiting an increase in blood glucose levels.

Besides the surprising finding that metabolites could be shown to be risk markers for the development of T2D, an equally important finding is that all metabolites identified as risk factors share the common characteristic of being decoupled from the common risk factor of increased blood glucose levels. In other words, the above described disturbances in amounts of said one or more metabolite(s) of the first and/or second group can be detected prior to any increase in blood glucose levels of a subject. An increase in blood glucose levels is defined to be an increase above $HbA_{1c}>5.7\%$, wherein a $HbA_{1c} \geq 6.5\%$ is associated with T2D (ADA (2010) Executive summary: Standards of medical care in diabetes—2010. Diabetes Care 33 Suppl 1: S4-10). The increase in blood glucose level can be due to either pre-diabetes (IGT) or due to i-IFG.

In another preferred embodiment of the methods of the invention, the method is performed at least every two years.

It is understood in accordance with the invention that the above described disturbances in amounts of said one or more metabolite(s) of the first and/or second group can occur at different time points prior to a subject developing an impaired glucose tolerance that is associated with the risk to develop T2D, therefore the method of the invention may need to be performed at certain intervals such as, e.g., at least every year, at least once in two years, at least once in (for each value) 3, 4, 5, 6, 7 or at least once in 8 or more years as a means to monitor the metabolite amount(s). In other words, performing the method of identifying in accordance with the invention only once in a sample from a given subject does not provide a terminal assessment of the risk to develop T2D, because changes in the amounts of said one or more metabolite(s) identified by the inventors may develop over time and thus may not be present at the time of performing the method of the invention for the first time. Thus, and if said first test is negative, i.e. the person is determined to be not at risk to develop T2D, said subject should nevertheless be monitored as described herein-above. The intervals at which subsequent tests according to the method of the invention are to be performed may depend on factors such as, e.g., the choice of metabolite(s) whose amount is to be assessed, the age or physical constitution of a subject. For example, in the case of only assessing the amount of one metabolite said intervals between testing should generally be shorter as when relying on more metabolites for making a risk prediction, but this may depend also on the chosen metabolite. For example, when only relying on acetylcarnitine C2 or an isobaric metabolite having the same molecular weight as acetylcarnitine C2 but different chemical formula one may have to repeat testing at least once every two years, whereas relying on glycine and/or lysoPhosphatidylcholine acyl C18:2 may warrant testing only at least once in 7 years. To increase the predictive power of the method of the invention it is envisioned to assess the amount of more than one metabolite in accordance with the invention, although the assessment of one metabolite defined herein is sufficient. For example, the amount of at least 2, such as at least (for each value) 3, 4, more preferred at least (for each value) 5, 6, and most preferred at least (for each value) 7, 8 or 9, i.e. all metabolites (excluding isobaric metabolites) of said first and second group is assessed. Of course, it is also envisioned that a mixture including isobaric metabolites or only one or more isobaric metabolite(s) of said first and/or second group are assessed.

In a different preferred embodiment of the methods of the invention, said one or more metabolite(s) are selected from lysoPhosphatidylcholine acyl C17:0, lysoPhosphatidylcholine acyl C18:0, lysoPhosphatidylcholine acyl C18:2, glycine and isobaric metabolites having the same molecular weight as lysoPhosphatidylcholine acyl C17:0, lysoPhosphatidylcholine acyl C18:0, lysoPhosphatidylcholine acyl C18:2 or glycine but a different chemical formula of said first group of metabolites and acetylcarnitine C2 and an isobaric metabolite having the same molecular weight as acetylcarnitine C2 but a different chemical formula of said second group of metabolites.

Each of the above mentioned metabolites has been shown to be particularly predictive for the development of T2D as well as IGT. Set out below are specific combinations of metabolites that together provide for a particularly improved prediction of IGT and T2D as compared to state of the art T2D risk indicators. As can be seen from FIGS. 3 and 4, certain combinations provide a significantly improved predictive value in comparison to state of the art predictive T2D markers.

In another preferred embodiment of the invention, said one or more metabolite(s) are selected from lysoPhosphatidylcholine acyl C18:2, glycine and isobaric metabolites having the same molecular weight as lysoPhosphatidylcholine acyl C18:2 or glycine but a different chemical formula of said first group of metabolites and acetylcarnitine C2 and an isobaric metabolite having the same molecular weight as acetylcarnitine C2 but a different chemical formula of said second group of metabolites.

In further preferred embodiment of the methods of the invention, wherein the amount of the metabolites glycine and lysoPhosphatidylcholine acyl C18:2 or isobaric metabolites having the same molecular weight as glycine and lysoPhosphatidylcholine acyl C18:2 but different chemical formula is assessed; wherein the amount of three metabolites selected from the group comprising glycine, lysoPhosphatidylcholine acyl C18:2 and acetylcarnitine C2 or isobaric metabolites having the same molecular weight as glycine, lysoPhosphatidylcholine acyl C18:2 and acetylcarnitine C2 but different chemical formula is assessed; wherein the amount of four metabolites selected from the group comprising glycine, lysoPhosphatidylcholine acyl C18:2, acetylcarnitine C2 and phosphatidylcholine acyl-alkyl C34:2 or isobaric metabolites having the same molecular weight as glycine, lysoPhosphatidylcholine acyl C18:2, acetylcarnitine C2 and phosphatidylcholine acyl-alkyl C34:2 but different chemical formula is assessed; or wherein the amount of five metabolites selected from the group comprising glycine, lysoPhosphatidylcholine acyl C18:2, acetylcarnitine C2, phosphatidylcholine acyl-alkyl C34:2 and lysoPhosphatidylcholine acyl C17:0 or isobaric metabolites having the same molecular weight as glycine, lysoPhosphatidylcholine acyl C18:2, acetylcarnitine C2, phosphatidylcholine acyl-alkyl C34:2 and lysoPhosphatidylcholine acyl C17:0 but different chemical formula is assessed.

In another preferred embodiment of the methods of the invention, the sample is selected from blood, serum or plasma.

One preferred sample to be used in the method of the invention is blood (cf. also supra) due to the ease of accessibility and clinical routine of blood collection as well as the standardized protocols to extract and, optionally, purify metabolites from blood constituents. Preferred in accordance with the method of the invention are peripheral blood mononuclear cells as a blood constituent that is to be further processed for extraction of metabolites. Serum as sample is preferred. Suitable methods for extraction and optional purification of metabolites from blood, serum or plasma are well-known to the person skilled in the art and exemplary methods are described herein.

Also envisioned as sample in accordance with the method of the invention are saliva and buccal smear samples that are equally conveniently accessible for collection, however, without having to injure a subject in order to get to the sample as compared to blood, serum or plasma collection. Preferred are buccal mucosa epithelial cells that can be isolated from buccal swabs for further processing to extract and, optionally, purify metabolites in order to assess amounts of metabolites associated with the risk to develop T2D.

In a further preferred embodiment of the methods of the invention, the assessment of the amount of said one or more metabolite(s) is effected by targeted or non-targeted NMR, FIA-MS, GC-MS or LC-MS.

For quantification of metabolite concentration, nuclear magnetic resonance (NMR) spectroscopy and mass spectrometry (MS) are the most widely used techniques (Suhre et al., *PloS one* 5, e13953 (2010)). NMR is the only detection technique which does not rely on separation of the analytes, and the sample can thus be recovered for further analyses. All kinds of small molecule metabolites can be measured simultaneously—in this sense, NMR is close to being a universal detector. The main advantages of NMR are high analytical reproducibility and simplicity of sample preparation. Practically, however, it is relatively insensitive compared to mass spectrometry-based techniques, and requires much larger (10-100×) sample volumes.

Mass spectrometry is used to identify and to quantify metabolites after separation by gas (GC) and liquid phase (LC) chromatography. MS is sensitive and can be very specific. MS based technologies are further classified as non-targeted approaches (e.g. GC-MS and LC-MS) and targeted metabolomics, which is based on pre-selected MRM pairs and isotope labeled internal standards, with many of their methods being based on rapid direct flow injection (FIA), however with capacity to carry out multiple GC-MS and LC-MS protocols. FIA-MS is especially adapted to high-throughput assays when large populations or time-series with many data points are investigated.

For example, and as described also in the example section, the targeted FIA- and LC-MS approached using the AbsoluteIDQ™ kit can be used for the assessment of metabolite amounts. The sample preparation was performed as described by manufacturer. Shortly (see also Römisch-Margl et al., Metabolomics 2012, 8(1):133-142), following sample preparation steps may be performed on a Hamilton ML Star robotics system (Hamilton Bonaduz A G, Bonaduz, Switzerland): (a) pipetting of 10 µl serum onto the filter inserts of the 96 well kit plate (containing stable isotope labeled internal standards), (b) drying of samples under nitrogen stream, (c) derivatization of amino acids with 5% phenylisothiocyanate reagent (PITC), (d) drying of samples, (e) extraction of metabolites and internal standards with 5 mM ammonium acetate in methanol, (f) centrifugation through filter membrane, (g) dilution with MS running solvent. The final extracts can be analyzed using an API 4000 triple quadrupole mass spectrometer (ABSciex) equipped with an Agilent 1200 Series HPLC and a HTC PAL auto sampler from CTC controlled by the software Analyst 1.5. The standard flow injection method comprising two 20 µL injections (one for positive and one for negative electrospray ionisation mode) can be applied for all measurements. Quantification can be achieved by multiple reaction monitoring (MRM) detection in combination with the use of stable isotope-labeled and other internal standards. Data evaluation for quantification of metabolite concentrations can then be performed with the MetIQ™ software package (integral part of the AbsoluteIDQ™ kit). Concentrations of all metabolites can initially be calculated in µM. The exemplary method is proven to be in conformance with FDA Guidelines (U.S. Department of Health and Human Services 2001), which imply proof of reproducibility within a given error range.

In a different preferred embodiment of the method of identifying a compound capable of preventing type 2 diabetes mellitus and diseases associated therewith or serving as a lead compound for developing a compound capable of preventing type 2 diabetes mellitus and diseases associated therewith, said test compound is selected from a small molecule, an antisense nucleic acid molecule, a siRNA, a shRNA, a miRNA, a ribozyme, a peptide aptamer, a nucleic acid based aptamer, an antibody or a combination thereof.

The term "small molecule" as used herein may describe, for example, a small organic molecule. Organic molecules relate or belong to the class of chemical compounds having a carbon basis, the carbon atoms linked together by carbon-carbon bonds. The original definition of the term organic related to the source of chemical compounds, with organic compounds being those carbon-containing compounds obtained from plant or animal or microbial sources, whereas inorganic compounds were obtained from mineral sources. Organic compounds can be natural or synthetic. Alternatively the compound may be an inorganic compound. Inorganic compounds are derived from mineral sources and include all compounds without carbon atoms (except carbon dioxide, carbon monoxide and carbonates). Preferably, the small molecule has a molecular weight of less than about 2000 amu, or less than about 1000 amu such as 500 amu, and even less than about 250 amu. The size of a small molecule can be determined by methods well-known in the art, e.g., mass spectrometry. Small molecules may be designed, for example, in silico based on the crystal structure of potential drug targets, where sites presumably responsible for the biological activity and involved in the modulation of metabolite amount(s) identified herein, can be identified and verified in in vivo assays such as in vivo HIS (high-throughput screening) assays.

The term "antisense nucleic acid molecule" is known in the art and refers to a nucleic acid which is complementary to a target nucleic acid. An antisense molecule according to the invention is capable of interacting with, more specifically hybridizing with the target nucleic acid. By formation of the hybrid, transcription of the target gene(s) and/or translation of the target mRNA is reduced or blocked. Preferably, the nucleic acid molecule is a antisense RNA molecule. Standard methods relating to antisense technology have been described (see, e.g., Melani et al., Cancer Res. (1991) 51:2897-2901).

For therapeutic uses, the RNA inactivation by antisense molecules or by ribozymes (cf. infra) appears to be implementable. Both classes of compounds can be synthesized chemically or produced in conjunction with a promoter by biological expression in vitro or even in vivo.

Small interfering RNAs (siRNA), sometimes known as short interfering RNAs or silencing RNAs, are a class of 18 to 30, preferably 20 to 25, most preferred 21 to 23 or 21 nucleotide-long double-stranded RNA molecules that play a variety of roles in biology. Most notably, siRNA is involved in the RNA interference (RNAi) pathway where the siRNA interferes with the expression of a specific gene. In addition to their role in the RNAi pathway, siRNAs also act in RNAi-related pathways, e.g. as an antiviral mechanism or in shaping the chromatin structure of a genome.

Said siRNA molecule or a metabolic processing product thereof is capable of mediating target-specific nucleic acid modifications, particularly RNA interference and/or DNA methylation. Preferably at least one RNA strand has a 5'- and/or 3'-overhang. Preferably, one end of the double-strand has a 3'-overhang from 1-5 nucleotides, more preferably from 1-3 nucleotides and most preferably 2 nucleotides. The other end may be blunt-ended or has up to 6 nucleotides 3'-overhang. In general, any RNA molecule suitable to act as siRNA is envisioned in the present invention.

Preferred siRNAs have a well defined structure: a short double-strand of RNA (dsRNA) with 2-nt 3' overhangs on either end. Each strand has a 5' phosphate group and a 3' hydroxyl (—OH) group. As regards naturally occurring siRNAs, this structure is the result of processing by dicer, an enzyme that converts either long dsRNAs or small hairpin RNAs into siRNAs. SiRNAs can also be exogenously (artificially) introduced into cells to bring about the specific knockdown of a gene of interest. Essentially any gene of which the sequence is known can thus be targeted based on sequence complementarity with an appropriately tailored siRNA.

The most efficient silencing was so far obtained with siRNA duplexes composed of 21-nt sense and 21-nt antisense strands, paired in a manner to have a 2-nt 3'-overhang. The sequence of the 2-nt 3' overhang makes a small contribution to the specificity of target recognition restricted to the unpaired nucleotide adjacent to the first base pair (Elbashir et al., EMBO J 2001, 20(23):6877-6888). 2'-deoxynucleotides in the 3' overhangs are as efficient as ribonucleotides, but are often cheaper to synthesize and probably more nuclease resistant.

A short hairpin RNA (shRNA) is a sequence of RNA that makes a tight hairpin turn that can be used to silence gene expression via RNA interference. shRNA uses a vector introduced into cells and utilizes the U6 promoter to ensure that the shRNA is always expressed. This vector is usually passed on to daughter cells, allowing the gene silencing to be inherited. The shRNA hairpin structure is cleaved by the cellular machinery into siRNA, which is then bound to the RNA-induced silencing complex (RISC). This complex binds to and cleaves mRNAs which match the siRNA that is bound to it.

Si/shRNAs to be used in the method of the present invention are preferably chemically synthesized using appropriately protected ribonucleoside phosphoramidites and a conventional DNA/RNA synthesizer. Suppliers of RNA synthesis reagents are Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA), and Cruachem (Glasgow, UK). Most conveniently, siRNAs are obtained from commercial RNA oligo synthesis suppliers, which sell RNA-synthesis products of different quality and costs. In general, the RNAs applicable in the present invention are conventionally synthesized and are readily provided in a quality suitable for RNAi.

Further molecules effecting RNAi include, for example, microRNAs (miRNA). Said RNA species are single-stranded RNA molecules which as endogenous RNA molecules regulate gene expression. Upon binding to a complementary mRNA transcript triggers the degradation of said mRNA transcript through a process similar to RNA interference. Accordingly, miRNAs may be employed to directly or indirectly regulate the amounts of metabolites associated with the risk to develop T2D as defined herein.

A "ribozyme" (from ribonucleic acid enzyme, also called RNA enzyme or catalytic RNA) is an RNA molecule that catalyzes a variety of reactions. Many natural ribozymes catalyze either their own cleavage or the cleavage of other RNAs, but they have also been found to catalyze the aminotransferase activity of the ribosome.

Examples of well-characterized small self-cleaving RNAs are the hammerhead, hairpin, hepatitis delta virus, and in vitro-selected lead-dependent ribozymes. The organization of these small catalysts is contrasted to that of larger ribozymes, such as the group I intron.

The principle of catalytic self-cleavage has become well established in the last 10 years. The hammerhead ribozymes are characterized best among the RNA molecules with ribozyme activity. Since it was shown that hammerhead structures can be integrated into heterologous RNA sequences and that ribozyme activity can thereby be transferred to these molecules, it appears that catalytic antisense sequences for almost any target sequence can be created, provided the target sequence contains a potential matching cleavage site.

The basic principle of constructing hammerhead ribozymes is as follows: An interesting region of the RNA, which contains the GUC (or CUC) triplet, is selected. Two oligonucleotide strands, each with 6 to 8 nucleotides, are taken and the catalytic hammerhead sequence is inserted between them. Molecules of this type were synthesized for numerous target sequences. They showed catalytic activity in vitro and in some cases also in vivo. The best results are usually obtained with short ribozymes and target sequences.

Aptamers are oligonucleic acid or peptide molecules that bind a specific target molecule. Aptamers are usually created by selecting them from a large random sequence pool, but natural aptamers also exist in riboswitches. Aptamers can be used for both basic research and clinical purposes as macromolecular drugs. Further, they can be combined with ribozymes to self-cleave in the presence of their target molecule.

More specifically, aptamers can be classified as DNA or RNA aptamers or peptide aptamers. Whereas the former consist of (usually short) strands of oligonucleotides, the latter consist of a short variable peptide domain, attached at both ends to a protein scaffold.

Nucleic acid aptamers are nucleic acid species that may be engineered through repeated rounds of in vitro selection or equivalently, SELEX (systematic evolution of ligands by exponential enrichment) to bind to various molecular targets such as small molecules, proteins, nucleic acids, and even cells, tissues and organisms.

Peptide aptamers are proteins that are designed to interfere with other protein interactions inside cells. They consist of a variable peptide loop attached at both ends to a protein scaffold. This double structural constraint greatly increases the binding affinity of the peptide aptamer to levels comparable to an antibody's (nanomolar range). The variable loop length is typically comprised of 10 to 20 amino acids, and the scaffold may be any protein which have good solubility properties. Currently, the bacterial protein Thioredoxin-A is the most used scaffold protein, the variable loop being inserted within the reducing active site, which is a -Cys-Gly-Pro-Cys-loop in the wild protein, the two cysteines lateral chains being able to form a disulfide bridge. Peptide aptamer selection can be made using different systems, but the most used is currently the yeast two-hybrid system.

Aptamers offer the utility for biotechnological and therapeutic applications as they offer molecular recognition properties that rival those of the commonly used biomolecules, in particular antibodies. In addition to their discriminate recognition, aptamers offer advantages over antibodies as they can be engineered completely in a test tube, are readily produced by chemical synthesis, possess desirable storage properties, and elicit little or no immunogenicity in therapeutic applications.

Non-modified aptamers are cleared rapidly from the bloodstream, with a half-life of minutes to hours, mainly due to nuclease degradation and clearance from the body by the kidneys, a result of the aptamer's inherently low molecular weight. Unmodified aptamer applications currently focus on treating transient conditions such as blood clotting, or treating organs such as the eye where local delivery is possible. This rapid clearance can be an advantage in applications such as in vivo diagnostic imaging. Several modifications, such as 2'-fluorine-substituted pyrimidines, polyethylene glycol (PEG) linkage, etc. are available to scientists with which the half-life of aptamers easily can be increased to the day or even week time scale.

A recent development is the combination of an aptamer recognizing a small compound with a hammerhead ribozyme. The conformational change induced in the aptamer upon binding the target molecule, is supposed to regulate the catalytic function of the ribozyme.

The term "antibody" as used herein can be, for example, relate to polyclonal or monoclonal antibodies. The term "antibody" also comprises derivatives or fragments thereof with retained binding specificity. Techniques for the production of antibodies are well known in the art and described, e.g. in Harlow and Lane "Antibodies, A Laboratory Manual", Cold Spring Harbor Laboratory Press, 1988 and Harlow and Lane "Using Antibodies: A Laboratory Manual" Cold Spring Harbor Laboratory Press, 1999. The antibodies can be used in accordance with the method of the invention to modulate the amount of any metabolite associated with a risk to develop T2D described herein. Also, antibodies may be useful, for example, for immunoprecipitation, affinity purification and immunolocalization of the gene products, i.e. the proteins, of the genes associated with a risk to develop T2D as well as for the monitoring of the presence and amount of such proteins, for example, in cultures of eukaryotic cells or organisms.

An antibody to be used in accordance with the invention also includes embodiments such as chimeric (human constant domain, non-human variable domain), single chain and humanized (human antibody with the exception of non-human CDRs) antibodies, as well as antibody fragments, like, inter alia, Fab or Fab' fragments. Antibody fragments or derivatives further comprise Fd, F(ab')2, Fv or scFv fragments; see, for example, Harlow and Lane (1988) and (1999), loc. cit. Various procedures are known in the art and may be used for the production of such antibodies and/or fragments. For example, the (antibody) derivatives can be produced by peptidomimetics. Further, techniques described for the production of single chain antibodies (see, inter alia, U.S. Pat. No. 4,946,778) can be adapted to produce single chain antibodies specific for any target epitope/s. Also, transgenic animals or plants (see, e.g., U.S. Pat. No. 6,080, 560) may be used to express (humanized) antibodies specific for any target epitope/s. For the preparation of monoclonal antibodies, any technique which provides antibodies produced by continuous cell line cultures can be used. Examples for such techniques include the hybridoma technique (Köhler and Milstein, Nature 256 (1975), 495-497), the trioma technique, the human B-cell hybridoma technique (Kozbor, Immunology Today 4 (1983), 72) and the EBV-hybridoma technique to produce human monoclonal antibodies (Cole et al., Monoclonal Antibodies and Cancer Therapy, Alan R. Liss, Inc. (1985), 77-96). Surface plasmon resonance as employed in the BIAcore system can be used to increase the efficiency of phage antibodies which bind to an epitope of an polypeptide of the invention (Schier, Human Antibodies Hybridomas 7 (1996), 97-105; Malmborg, J. Immunol. Methods 183 (1995), 7-13). It is also envisaged in the context of this invention that the term "antibody" comprises antibody constructs which may be expressed in cells, e.g. antibody constructs which may be transfected and/or transduced via, amongst others, viruses or plasmid vectors.

The antibody to be used in the method of the invention is capable to specifically bind/interact with a target epitope. The term "specifically binding/interacting with" as used in accordance with the present invention means that the antibody does not or essentially does not cross-react with an epitope of similar structure. Cross-reactivity of a panel of antibodies under investigation may be tested, for example, by assessing binding of said panel of antibodies under conventional conditions to the epitope of interest as well as to a number of more or less (structurally and/or functionally) closely related epitopes. Only those antibodies that bind to the epitope of interest in its relevant context (e.g. a specific motif in the structure of a protein) but do not or do not essentially bind to any of the other epitope are considered specific for the epitope of interest and thus to be antibodies in accordance with this invention. Corresponding methods are described e.g. in Harlow and Lane, 1988 and 1999, loc cit.

As outlined herein above, metabolite amounts can be significantly influenced by targeting, e.g., regulatory or enzymatically active proteins in the metabolic pathway of a given metabolite identified herein as risk factor for developing T2D. Therefore, it will be possible to decrease or increase the amount of said given metabolite by using, e.g., the above described antisense nucleic acid molecule, the RNA molecules or antibodies targeting said regulatory or enzymatically active proteins or the genes encoding them. Said compounds may be designed by methods well-known in the art to interact target-specifically with either mRNA or protein molecules of said regulatory or enzymatically active proteins and thereby, indirectly, reduce the metabolite amounts of one or more metabolite(s) identified herein as risk factors. For example, RNA molecules suitable for RNA interference can be designed leading to a reduction of mRNA molecules and hence of the expression level of the targeted gene(s) encoding said regulatory or enzymatically active proteins. However, it may also be possible to reduce or increase the expression level of said targeted gene(s) by using any of the above-mentioned compounds by reducing and/or inhibiting, e.g., protein or mRNA molecules that are involved in the regulation of expression of said targeted gene(s). Metabolites may also be directly targeted when using, e.g. antibodies, to decrease the amount of metabolites of the second group defined herein above.

It is further understood in accordance with the invention that an increase or decrease in the amount of a given metabolite may (only) be achievable when combining several (different) of the above described compounds. Thus, it is envisage that a combination of said test compounds are used in the method of the invention and contacted simultaneously with a cell or a test sample obtained from a subject.

In a further embodiment, the invention relates to a method of selecting a therapy to prevent type 2 diabetes mellitus comprising the steps of: (a) identifying a predisposition for developing type 2 diabetes mellitus according to any one of claims 1, 4 to 10; and (b) selecting a therapy based on the results obtained in the preceding step.

As is evident to the person skilled in the art, the knowledge deduced from the present invention can now be used to exactly and reliably characterize the metabolite profile of a subject as far as it is relevant in the identification of a predisposition to develop T2D. Advantageously, T2D can be predicted and preventive measures can be applied accordingly. Moreover in accordance with the foregoing, in cases where a given therapy (such as, metformin regimen, increase in physical activity and/or weight loss) proves to be not effective, a suitable individual therapy can be designed based on the knowledge of the individual metabolite profile of a subject with respect to the metabolites associated with a risk to develop T2D and new and/or improved therapeutics can be identified, for example, by the method of the invention, and/or developed as has been discussed supra.

As outlined above, a reliable method to identify a predisposition to develop T2D independent from the occurrence of increased glucose levels, such as can be the case for impaired glucose tolerance has not been available prior to the present invention. Hence, an early diagnosis of a predisposition potentially demands for a different therapy than treating symptoms associated with impaired glucose tolerance in an afflicted subject.

In conclusion, due to the invention it is possible to select a suitable medical intervention such as, e.g., a drug treatment and/or changes in lifestyle (such as, e.g., dietary changes), having overall a more beneficial effect than medical approaches without having regard to the individual metabolic profile of the metabolites associated with a risk to develop T2D. The effects of therapies, e.g., pharmacologic effects of drugs, can be determined by methods well-known in the art and include, for example, in vitro methods or collecting data relating to disease symptoms in a patient or group of patients.

In a preferred embodiment of the method for selecting a therapy, said method comprises i) prior to step (b) a further step (a') of applying and monitoring a therapy; and/or ii) after step (b) a further step (b') of monitoring the therapy selected in step (b).

The method of selecting a therapy may comprise the additional step (a') of applying and monitoring a therapy and based on its outcome select a therapy. For example, subjects that are diagnosed to be at risk for developing T2D and put on a prophylactic therapy can be monitored, recorded and, if necessary (the selection (b) also encompasses not changing the therapy), their therapy subsequently be adjusted or changed, corresponding to the selection step (b), depending on whether further risk factors of T2D occur and to which extent or not. The recorded data provides the basis for the assessment whether the therapy applied is beneficial to the patient or not. Based on said assessment the person skilled in the art, in this case likely a clinician, will be able to adjust the currently applied therapy, e.g., by increasing/decreasing dosage regimen or dosage amount of the therapy, and/or suggesting further changes to the patient's lifestyle, or decide to completely switch to another therapy, e.g. based on different therapeutically active compounds. The above applies mutatis mutandis, if as an alternative to step (a') or in addition to step (a') a further step (b') of monitoring the therapy selected in step (b) is performed.

In a further embodiment, the invention relates to a kit comprising or consisting of stable isotope-labelled glycine, stable isotope-labelled lysoPhosphatidylcholine acyl C18:2, stable isotope-labelled lysoPhosphatidylcholine acyl C17:0, stable isotope-labelled lysoPhosphatidylcholine acyl C18:0, stable isotope-labelled lysoPhosphatidylcholine acyl C18:1, stable isotope-labelled phosphatidylcholine acyl-alkyl C34:2, stable isotope-labelled phosphatidylcholine acyl-alkyl C36:2, stable isotope-labelled phosphatidylcholine acyl-alkyl C36:3 and/or stable isotope-labelled acetylcarnitine C2;

stable isotope-labelled isobaric metabolites having the same molecular mass as glycine, lysoPhosphatidylcholine acyl C18:2, lysoPhosphatidylcholine acyl C17:0, lysoPhosphatidylcholine acyl C18:0, lysoPhosphatidylcholine acyl C18:1, phosphatidylcholine acyl-alkyl C34:2, phosphatidylcholine acyl-alkyl C36:2, phosphatidylcholine acyl-alkyl C36:3 and/or acetylcarnitine C2 but different chemical formula; and/or compounds not naturally occurring in a human sample and chemically similar to glycine, lysoPhosphatidylcholine acyl C18:2, lysoPhosphatidylcholine acyl C17:0, lysoPhosphatidylcholine acyl C18:0, lysoPhosphatidylcholine acyl C18:1, phosphatidylcholine acyl-alkyl C34:2, phosphatidylcholine acyl-alkyl C36:2, phosphatidylcholine acyl-alkyl C36:3, and/or acetylcarnitine C2.

Preferably, the kit consist of or comprises stable isotope-labelled glycine, stable isotope-labelled lysoPhosphatidylcholine acyl C18:2, stable isotope-labelled lysoPhosphatidylcholine acyl C17:0, stable isotope-labelled lysoPhosphatidylcholine acyl 018:0, stable isotope-labelled lysoPhosphatidylcholine acyl C18:1, stable isotope-labelled phosphatidylcholine acyl-alkyl C34:2, stable isotope-labelled phosphatidylcholine acyl-alkyl C36:2, stable isotope-labelled phosphatidylcholine acyl-alkyl C36:3 and/or stable isotope-labelled acetylcarnitine C2.

For example, the kit may comprise the combinations of:

stable isotope-labelled glycine and stable isotope-labelled lysoPhosphatidylcholine acyl C18:2;

stable isotope-labelled isobaric metabolites having the same molecular weight as glycine and lysoPhosphatidylcholine acyl C18:2 but a different chemical formula;

compounds not naturally occurring in a human sample and chemically similar to glycine and lysoPhosphatidylcholine acyl C18:2;

stable isotope-labelled glycine, stable isotope-labelled lysoPhosphatidylcholine acyl C18:2 and stable isotope-labelled acetylcarnitine C2;

stable isotope-labelled isobaric metabolites having the same molecular weight as glycine, lysoPhosphatidylcholine acyl C18:2 and acetylcarnitine C2 but a different chemical formula; compounds not naturally occurring in a human sample and chemically similar to glycine, lysoPhosphatidylcholine acyl C18:2 and acetylcarnitine C2;

stable isotope-labelled glycine, stable isotope-labelled lysoPhosphatidylcholine acyl C18:2, stable isotope-labelled acetylcarnitine C2 and stable isotope-labelled phosphatidylcholine acyl-alkyl C34:2;

stable isotope-labelled isobaric metabolites having the same molecular weight as glycine, lysoPhosphatidylcholine acyl C18:2, acetylcarnitine C2 and phosphatidylcholine acyl-alkyl C34:2 but a different chemical formula;

compounds not naturally occurring in a human sample and chemically similar to glycine, lysoPhosphatidylcholine acyl C18:2, acetylcarnitine C2 and phosphatidylcholine acyl-alkyl C34:2;

stable isotope-labelled glycine, stable isotope-labelled lysoPhosphatidylcholine acyl C18:2, stable isotope-labelled acetylcarnitine C2, stable isotope-labelled phosphatidylcholine acyl-alkyl C34:2 and stable isotope-labelled lysoPhosphatidylcholine acyl C17:0;

stable isotope-labelled isobaric metabolites having the same molecular weight as glycine, lysoPhosphatidylcholine acyl C18:2, acetylcarnitine C2, phosphatidylcholine acyl-alkyl C34:2 and lysoPhosphatidylcholine acyl C17:0 but a different chemical formula;

compounds not naturally occurring in a human sample and chemically similar to glycine, lysoPhosphatidylcholine acyl C18:2, acetylcarnitine C2, phosphatidylcholine acyl-alkyl C34:2 and lysoPhosphatidylcholine acyl C17:0.

Chemically similar compounds not naturally occurring in a given human sample include compounds that have for example a similar chemical formula, similar polarity or hydrophobicity, equal ionisation requirements, similar (but not identical) mass of precursor ion, and unique mass fragmentation spectrum as a given metabolite referred to herein above being used in the method of the invention. Non-limiting examples of chemically similar compounds not naturally occurring in said given human sample include for example carbamyloxyphosphatidylcholine, diacetylene modified phospholipids, 1,2-Dimyristoyl-sn-glycero-3-phosphorylcholine, or lipids with non-natural chain length, all of which are well known in the art and have been described, e.g. in Curatolo W, Bali A, Gupta C M (1985) Phase behavior of carbamyloxyphosphatidylcholine, a sphingolipid analogue. J Pharm Sci 74: 1255-1258, Dagan A, Wang C, Fibach E, Gatt S (2003) Synthetic, non-natural sphingolipid analogs inhibit the biosynthesis of cellular sphingolipids, elevate ceramide and induce apoptotic cell death. Biochim Biophys Acta 1633: 161-169, Navab M, Hama S, Hough G, Fogelman A M (2003) Oral synthetic phospholipid (DMPC) raises high-density lipoprotein cholesterol levels, improves high-density lipoprotein function, and markedly reduces atherosclerosis in apolipoprotein E-null mice. Circulation 108: 1735-1739, Qin J D, Weiss L, Slavin S, Gatt S, Dagan A (2010) Synthetic, non-natural analogs of ceramide elevate cellular ceramide, inducing apoptotic death to prostate cancer cells and eradicating tumors in mice. Cancer Invest 28: 535-543, Zumbuehl A (2009) Nonnatural Phospholipids: Probing Nature's Modular Platform. Chimia 63: 63-65.

Stable isotope-labelled metabolite standards have been described herein above. The kit of the present invention comprises three such stable isotope-labelled metabolite standards, suitable for the quantification of metabolite concentrations of SMOH C16:1, PCaa C36:2 and PCae C34:2 in a sample, such as for example a sample obtained from a woman suspected of having endometriosis.

The preparation, general use and data interpretation of stable isotope-labelled lipids are well known in the art and stable-isotopes can be identified by their increase in mass and unique isotope distribution (Postle A D (2012) Lipidomics. Current opinion in clinical nutrition and metabolic care 15: 127-133; Postle A D, Hunt A N (2009) Dynamic lipidomics with stable isotope labelling. Journal of chromatography B, Analytical technologies in the biomedical and life sciences 877: 2716-2721).

The components of the kit may be packaged in one or more containers such as one or more vials. In addition to the metabolite standards, the kit preferably further comprises preservatives or buffers for storage. In addition, the kit may contain instructions for use.

In a preferred embodiment of the kit of the invention, the isotope is selected from the group consisting of $^{12}C$, $^{13}C$, $^{14}N$, $^{15}N$ and $^{2}H$.

The present invention further relates to the use of the kit of the invention in a method of identifying a predisposition for developing type 2 diabetes mellitus in a subject in accordance with the present invention.

As regards the embodiments characterized in this specification, in particular in the claims, it is intended that each embodiment mentioned in a dependent claim is combined with each embodiment of each claim (independent or dependent) said dependent claim depends from. For example, in case of an independent claim 1 reciting 3 alternatives A, B and C, a dependent claim 2 reciting 3 alternatives D, E and F and a claim 3 depending from claims 1 and 2 and reciting 3 alternatives G, H and I, it is to be understood that the specification unambiguously discloses embodiments corresponding to combinations A, D, G; A, D, H; A, D, I; A, E, G; A, E, H; A, E, I; A, F, G; A, F, H; A, F, I; B, D, G; B, D, H; B, D, I; B, E, G; B, E, H; B, E, I; B, F, G; B, F, H; B, F, I; C, D, G; C, D, H; C, D, I; C, E, G; C, E, H; C, E, I; C, F, G; C, F, H; C, F, I, unless specifically mentioned otherwise.

Similarly, and also in those cases where independent and/or dependent claims do not recite alternatives, it is understood that if dependent claims refer back to a plurality of preceding claims, any combination of subject-matter covered thereby is considered to be explicitly disclosed. For example, in case of an independent claim 1, a dependent claim 2 referring back to claim 1, and a dependent claim 3 referring back to both claims 2 and 1, it follows that the combination of the subject-matter of claims 3 and 1 is clearly and unambiguously disclosed as is the combination of the subject-matter of claims 3, 2 and 1. In case a further dependent claim 4 is present which refers to any one of claims 1 to 3, it follows that the combination of the subject-matter of claims 4 and 1, of claims 4, 2 and 1, of claims 4, 3 and 1, as well as of claims 4, 3, 2 and 1 is clearly and unambiguously disclosed.

The above considerations apply mutatis mutandis to all attached claims.

The figures show:

FIG. 1: Population description.

Metabolomics screens in the KORA cohort, at baseline S4 (A), overlapped between S4 and F4 (B) and prospective (C and D). Participant numbers are shown. Normal glucose tolerance (NGT), isolated impaired fasting glucose (i-IFG), impaired glucose tolerance (IGT), type 2 diabetes mellitus (T2D) and newly diagnosed T2D (dT2D). Non-T2D individuals include NGT, i-IFG and IGT participants.

Figure 2:
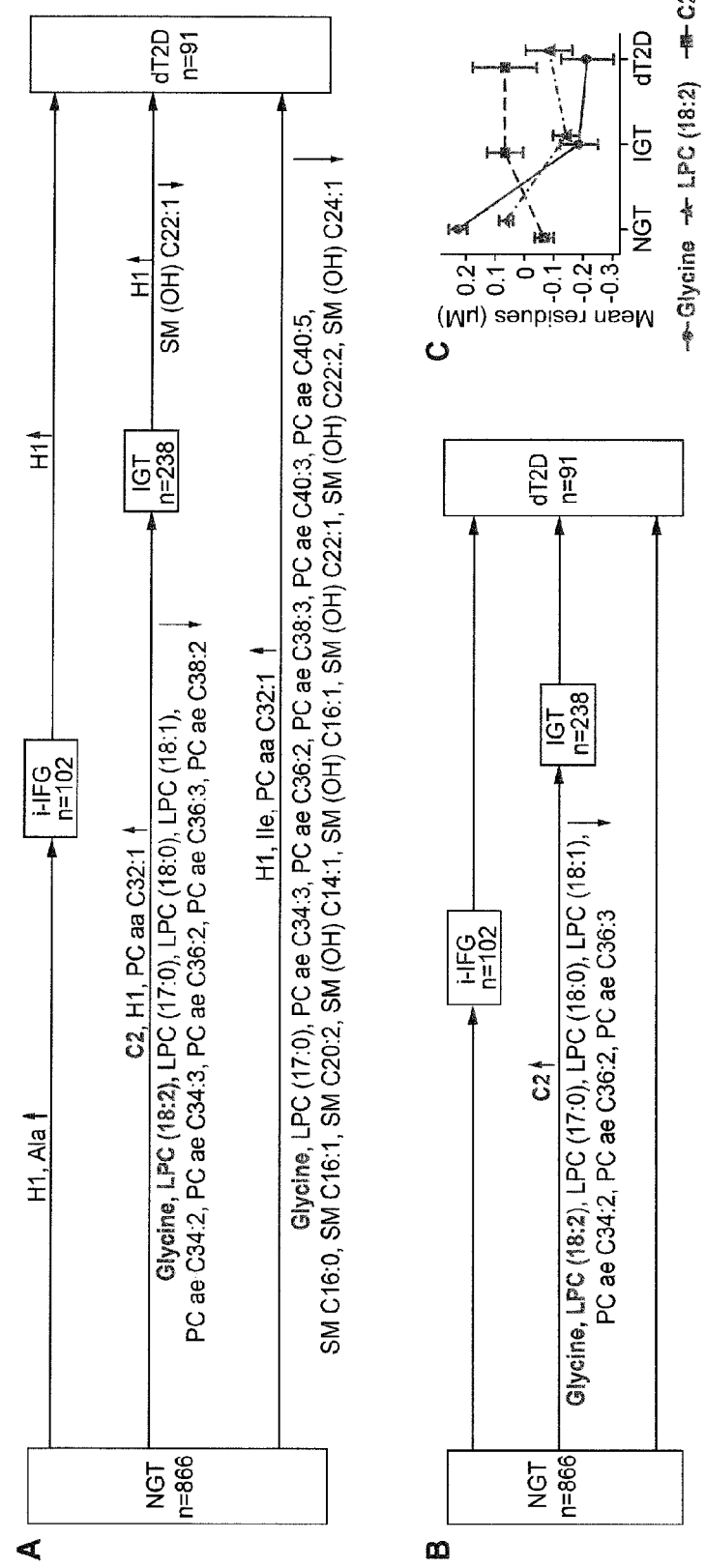

FIG. 2: Differences in metabolite concentrations from cross-sectional analysis.

Plots A and B show the names of metabolites with significantly different concentrations in multivariate logistic regression analyses (after the Bonferroni correction for multiple testing with $P<3.6\times10^{-4}$) in the five pairwise comparisons of model 1 and model 2. Plots C show the average residues of the concentrations with standard errors of the three metabolites (glycine, lysoPhosphatidylcholine acyl C18:2 (LPC (18:2)) and acetylcarnitine C2) for the NGT, IGT and dT2D groups. Plot A show the results with adjustment for model 1 (age, sex, BMI, physical activity, alcohol intake, smoking, systolic BP and HDL cholesterol), whereas plots B and C have additional adjustments for HbA1c, fasting glucose and fasting insulin (model 2). Residuals were calculated from linear regression model (formula: T2D status~metabolite concentration+model 2).

Figure 3:
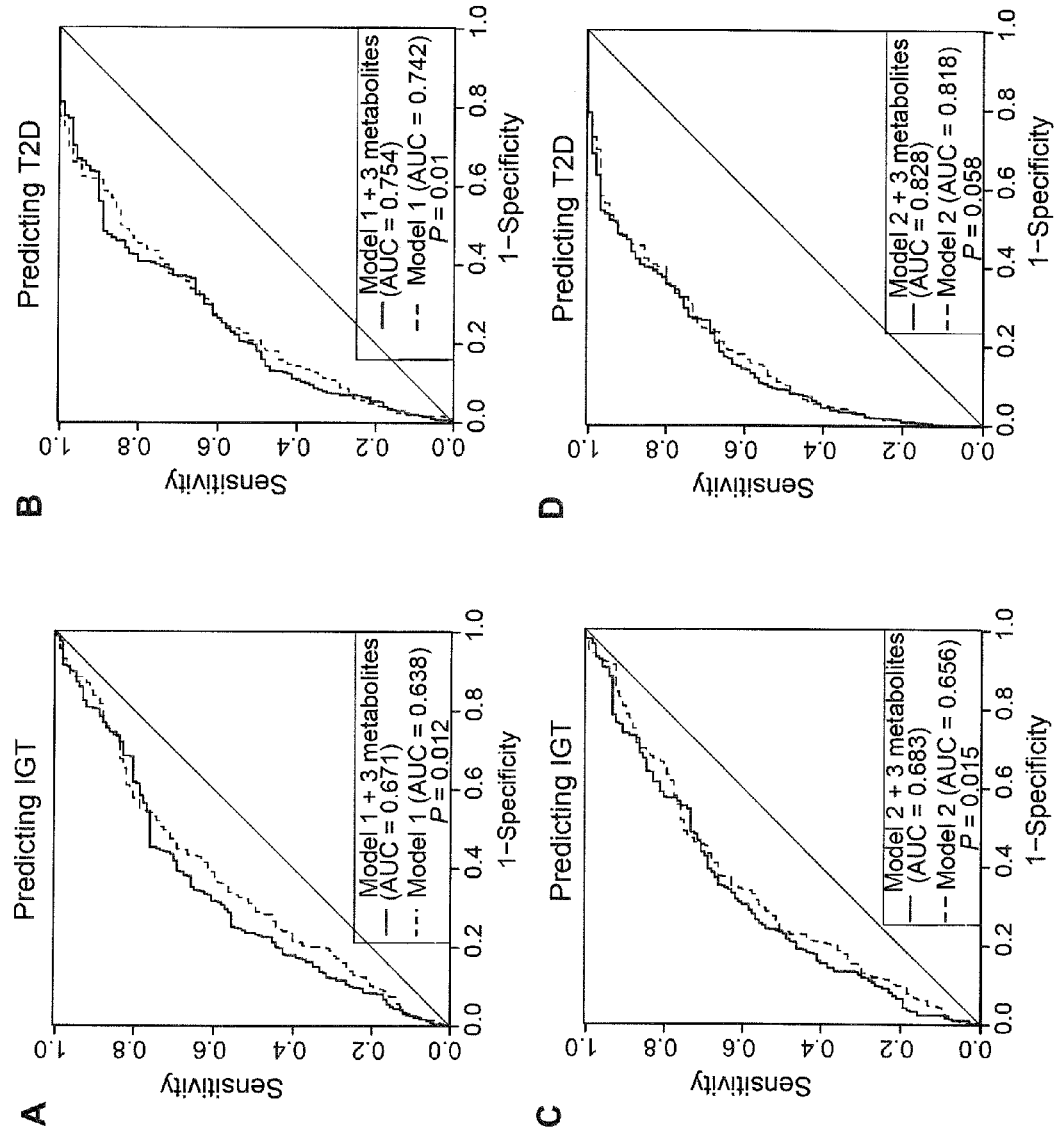

FIG. 3: Prospective analysis: prediction of IGT and T2D using two adjustment models.

Plots A-D show the AUC values predicting IGT or T2D using known T2D risk factors (model 1 or model 2) alone and in combination with three metabolites (glycine, LPC (18:2) and C2) and the P-values from likelihood ratio test comparing the two values.

Model 1 includes age, sex, BM1, physical activity, alcohol intake, smoking, systolic BP and HDL. Model 2 includes the risk factors from model 1 plus $HbA_{1c}$, fasting glucose and fasting insulin.

Figure 4:
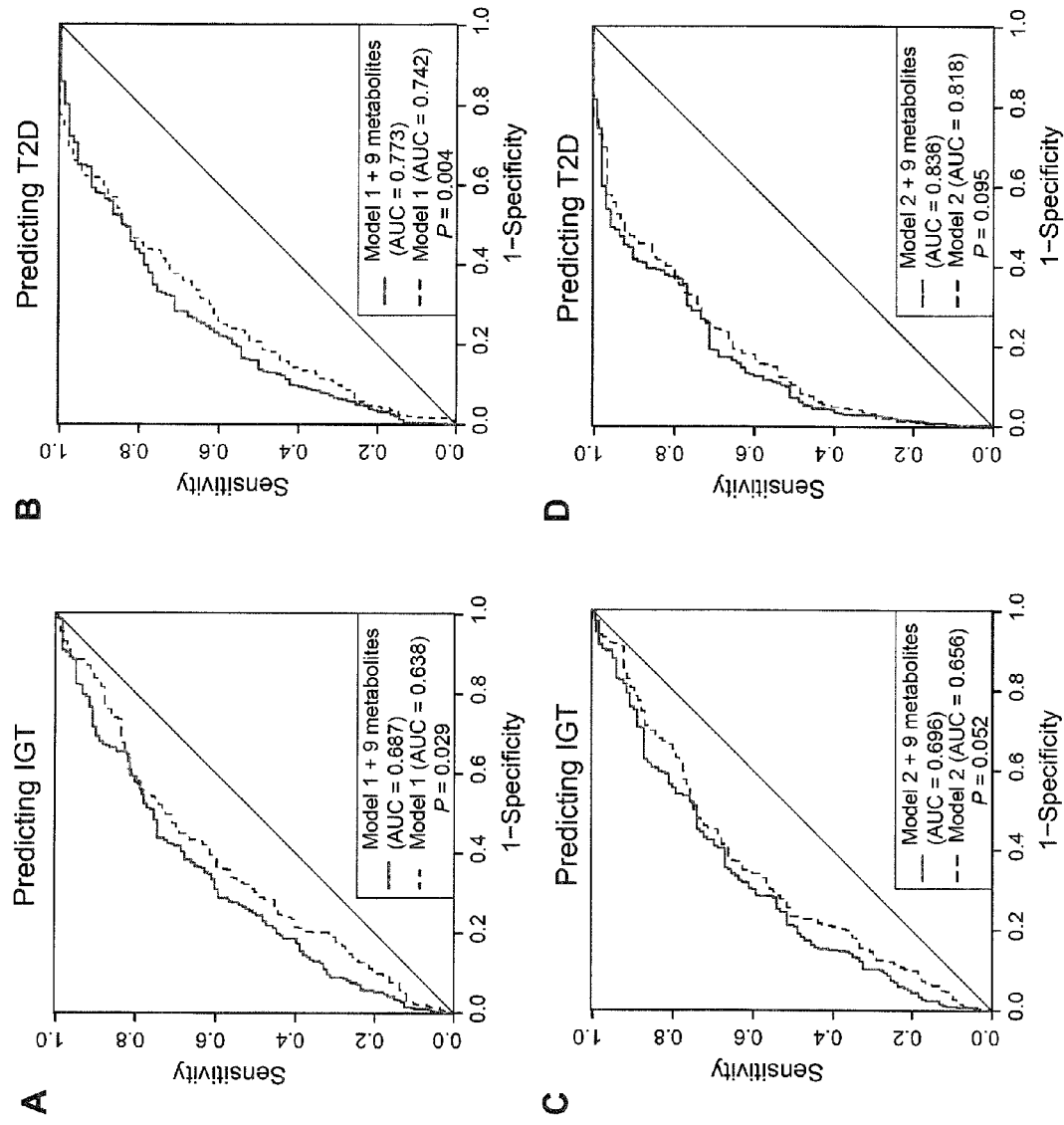

FIG. 4: Prospective analysis: prediction of IGT and T2D using two adjustment models combined with the nine metabolites.

Plots A-D show the AUC values predicting IGT or T2D using known T2D risk factors (model 1 or model 2) alone and in combination with nine metabolites (glycine, LPC (18:2), C2, LPC (17:0), LPC (18:0), LPC (18:1), PC ae C34:2, PC ae C36:2 and PC ae C36:3) and the P-values from likelihood ratio test comparing the two values.

Model 1 includes age, sex, BMI, physical activity, alcohol intake, smoking, systolic BP and HDL. Model 2 includes the risk factors from model 1 plus HbA1c, fasting glucose and fasting insulin The examples illustrate the invention:

EXAMPLE 1

Methods

Sample Source and Classification

The Cooperative Health Research in the Region of Augsburg (KORA) surveys are population-based studies conducted in the city of Augsburg and the surrounding towns and villages (Holle et al, 2005; Wichmann et al, 2005). KORA is a research platform in the field of epidemiology, health economics and health care research. Four surveys were conducted with 18 079 participants recruited from 1984 to 2001. The survey 4 (S4) consists of 4261 individuals (aged 25-74 years) examined from 1999 to 2001. From 2006 to 2008, 3080 participants (with an age range of 32-81) took part in a follow-up (F4) survey. Ascertainments of anthropometric measurements and personal interviews, as well as laboratory measurements of persons, from the KORA S4/F4 have been described elsewhere (Jourdan et al, PloS one 7: e40009 (2012); Meisinger et al, Diabet Med 27: 360-362 (2010); Rathmann et al, Diabet Med 26: 1212-1219 (2009)).

Sampling

In the KORA cohort, blood was drawn into S-Monovette® serum tubes (SARSTEDT AG & Co., Nümbrecht, Germany) in the morning between 8:00 and 10:30 am after at least 8 h of fasting. Tubes were gently inverted twice, followed by 30 min resting at room temperature, to obtain complete coagulation. For serum collection, blood was centrifuged at 2750 g at 15° C. for 10 min. Serum was filled into synthetic straws, which were stored in liquid nitrogen until the metabolic analyses were conducted.

Metabolite Measurements and Exclusion of Metabolites

For the KORA S4 survey, the targeted metabolomics approach was based on measurements with the Absolute/DQ™ p180 kit (BIOCRATES Life Sciences AG, Innsbruck, Austria). This method allows simultaneous quantification of 188 metabolites using liquid chromatography and flow injection analysis—mass spectrometry. The assay procedures have been described previously in detail (Wig et al, Nat Genet 42: 137-141 (2010); Romisch-Margl W et al, Metabolomics 2012, 8(1):133-142). For each kit plate, five references (human plasma pooled material, Seralab) and three zero samples (PBS) were measured in addition to the KORA samples. To ensure data quality, each metabolite had to meet two criteria: (1) the coefficient of variance (CV) for the metabolite in the total 110 reference samples had to be smaller than 25%. In total, seven outliers were removed because their concentrations were larger than the mean plus 5×SD; (2) 50% of all measured sample concentrations for the metabolite should be above the limit of detection (LOD), which is defined as 3× median of the three zero samples. In total, 140 metabolites passed the quality controls: one hexose (H1), 21 acylcarnitines, 21 amino acids, 8 biogenic amines, 13 sphingomyelins (SMs), 33 diacyl (aa) phosphatidylcholines (PCs), 35 acyl-alkyl (ae) PCs and 8 lysoPCs. Concentrations of all analyzed metabolites are reported in µM. Measurements of the 3080 KORA F4 samples and the involved cleaning procedure has already been described in detail (Mittelstrass et al, 2011; Yu et al, 2012).

Statistical Analysis

Calculations were performed under the R statistical environment (http://www.r-project.org/).

Multivariate Logistic Regression and Linear Regression

In multivariate logistic regression analysis, ORs for single metabolites were calculated between two groups. The concentration of each metabolite was scaled to have a mean of zero and a SD of one; thus, all reported OR values correspond to the change per SD of metabolite concentration. Various T2D risk factors were added to the logistic regression analysis as covariates. To handle false discovery rates from multiple comparisons, the cut-off point for significance was calculated according to the Bonferroni correction, at a level of $3.6 \times 10^{-4}$ (for a total use of 140 metabolites at the 5% level). Because the metabolites were correlated within well-defined biological groups (e.g. 8 lysoPCs, 33 diacyl PCs, 35 acyl-alkyl PCs and 13 SMs), this correction was conservative.

Additionally, the categorized metabolite concentrations and combined scores (see below) were analyzed, and ORs were calculated across quartiles. To test the trend across quartiles, we assigned all individuals either the median value of the concentrations or the combined scores, and obtained the P-values using the same regression model.

For linear regression analyses, beta estimates were calculated from the concentration of each metabolite and the 2-h glucose value. The concentration of each metabolite was log-transformed and normalized to have a mean of zero and a SD of one. Various risk factors in the logistic regression were added as covariates, and the same significance level $(3.6 \times 10^{-4})$ was adopted.

Combination of Metabolites

To obtain the combined scores of metabolites, the scaled metabolite concentrations (mean=0, SD=1) were first modeled with multivariate logistic regression containing all confounding variables. The coefficients of these metabolites from the model were then used to calculate a weighted sum for each individual. In accordance with the decreasing trend of glycine and LPC (18:2), we inverted these values as the combined scores.

Residuals of Metabolite Concentrations

To avoid the influence of other confounding factors when plotting the concentration of metabolites, the residuals from a linear regression model were used. Metabolite concentrations were log-transformed and scaled (mean=0, SD=1), and the residuals were then deduced from the linear regression that included the corresponding confounding factors.

Random Forest, Stepwise Selection Methods and Candidate Biomarker Selection

To select candidate biomarkers, two additional methods were applied: the random forest selection (Briman, 2001, Random Forests, Vol. Machine Learning: Kluwer Academic Publishers.) and the stepwise selection, which assess the metabolites as a group.

Between two groups, the supervised classification method of random forest was first used to select the metabolites among the 30 highest ranking variables of importance score, allowing the best separation of the individuals from different groups. T2D risk indicators were also included in this method with all the metabolites.

The metabolites were further selected using stepwise selection on the logistic regression model. Metabolites with significantly different concentrations between the compared groups in logistic regression, and which were also selected using random forest, were used in this model along with all the risk indicators. Akaike's Information Criterion (AIC) was used to evaluate the performance of these subsets of metabolites used in the models. The model with minimal AIC was chosen. The area under the receiver-operating-characteristic curves (AUC) was used to evaluate the models.

EXAMPLE 2

Identification of Risk Metabolites

Study Participants

Individuals with known T2D were identified by physician-validated self-reporting (Rathmann et al, 2010) and excluded from our analysis, to avoid potential influence from anti-diabetic medication with non-fasting participants and individuals with missing values (FIG. 1A). Based on both fasting and 2-h glucose values (i.e. two h post oral 75 g glucose load), individuals were defined according to the WHO diagnostic criteria to have normal glucose tolerance (NGT), isolated IFG (i-IFG), IGT or newly-diagnosed T2D (dT2D) (Meisinger et al, 2010; Rathmann et al, 2009; WHO, 1999) (see above). The sample sets include 91 newly-diagnosed T2D patients and 1206 individuals with non-T2D, including 866 participants with NGT, 102 with i-IFG and 238 with IGT, in the cross-sectional KORA S4 survey (FIG. 1A; study characteristics are shown in Table 1). Of the 1010 individuals in a fasting state who participated at baseline and follow-up surveys (FIG. 1B), 876 of them were non-diabetic at baseline. Out of these, about 10% developed T2D (i.e. 91 incident T2D) (FIG. 1C). From the 641 individuals with NGT at baseline, 18% developed IGT (i.e. 118 incident IGT) seven years later (FIG. 1D). The study characteristics of the prospective KORA S4→F4 are shown in Table 2.

TABLE 1

Characteristics of the KORA S4 cross-sectional study sample

| Clinical and laboratory parameters | NGT | i-IFG | IGT | dT2D |
|---|---|---|---|---|
| N | 866 | 102 | 238 | 91 |
| Age (years) | 63.5 ± 5.5 | 64.1 ± 5.2 | 65.2 ± 5.2 | 65.9 ± 5.4 |
| Sex (female) (%) | 52.2 | 30.4 | 44.9 | 41.8 |
| BMI (kg/m$^2$) | 27.7 ± 4.1 | 29.2 ± 4 | 29.6 ± 4.1 | 30.2 ± 3.9 |
| Physical activity (% >1 h per week) | 46.7 | 35.3 | 39.9 | 36.3 |
| Alcohol intake* (%): | 20.2 | 20.5 | 25.2 | 24.2 |
| Current smoker (%) | 14.8 | 10.8 | 10.9 | 23.1 |
| Systolic BP (mm-Hg) | 131.7 ± 18.9 | 138.9± | 140.7 ± 19.8 | 146.8 ± 21.5 |
| HDL cholesterol (mg/dl) | 60.5 ± 16.4 | 55.7 ± 15.9 | 55.7 ± 15.1 | 50.0 ± 15.8 |
| LDL cholesterol (mg/dl) | 154.5 ± 39.8 | 152.1± | 155.2 ± 38.6 | 146.1 ± 44.6 |
| Triglycerides (mg/dl) | 120.7 ± 68.3 | 145.0± | 146.6 ± 80.0 | 170.6± |
| HbA$_{1c}$ (%) | 5.56 ± 0.33 | 5.62 ± 0.33 | 5.66 ± 0.39 | 6.21 ± 0.83 |
| Fasting glucose (mg/dl) | 95.6 ± 7.1 | 114.2 ± 3.7 | 104.5 ± 9.7 | 133.2 ± 31.7 |
| 2-h glucose (mg/dl) | 102.1 ± 21.0 | 109.3± | 163.4 ± 16.4 | 232.1 ± 63.7 |
| Fasting insulin (µU/ml) | 10.48 ± 7.28 | 16.26± | 13.92 ± 9.53 | 17.70± |

*≥20 g/day for women; ≥40 g/day for men.

Abbreviations: NGT, normal glucose tolerance; i-IFG, isolated impaired fasting glucose; IGT, impaired glucose tolerance; dT2D, newly-diagnosed type 2 diabetes; BP, blood pressure; HDL, high-density lipoprotein; LDL, low-density lipoprotein. Percentages of individuals or means±SD are given for each variable and each group (NGT, i-IFG, IGT and dT2D).

TABLE 2

Characteristics of the KORA S4 → F4 prospective study samples

| | NGT at baseline (n = 589) | | Non-T2D at baseline (n = 876) | |
|---|---|---|---|---|
| | Remained NGT at follow-up | Developed IGT at follow-up | Remained Non-T2D at follow-up | Developed T2D at follow-up |
| N | 471 | 118 | 785 | 91 |
| Age (years) | 62.4 ± 5.4 | 63.9 ± 5.5 | 62.9 ± 5.4 | 65.5 ± 5.2 |
| Sex (female) (%) | 52.2 | 55.9 | 50.8 | 34.1 |
| BMI (kg/m$^2$) | 27.2 ± 3.8 | 28.2 ± 3.9 | 27.9 ± 4 | 30.2 ± 3.6 |
| Physical activity (% >1 h per week) | 52.9 | 43.2 | 52.2 | 58.2 |
| Alcohol intake* (%) | 19.9 | 20.3 | 20.6 | 19.8 |
| Smoker (%) | 14.6 | 9.3 | 12.0 | 14.3 |
| Systolic BP (mm-Hg) | 129.6 ± 18.2 | 134.2 ± 18.7 | 132.4 ± 18.6 | 137.8 ± 19 |
| HDL cholesterol (mg/dl) | 61.3 ± 16.8 | 58.9 ± 16.2 | 60.0 ± 16.5 | 51.9 ± 12.4 |
| LDL cholesterol (mg/dl) | 153.9 ± 38.4 | 156.9 ± 42.7 | 154.5 ± 39.5 | 157.7 ± 41.6 |
| Triglycerides (mg/dl) | 118.1 ± 63.9 | 129.5 ± 79.0 | 125.0 ± 70.0 | 151.2 ± 74.2 |
| HbA$_{1c}$ (%) | 5.54 ± 0.33 | 5.59 ± 0.34 | 5.6 ± 0.3 | 5.8 ± 0.4 |
| Fasting glucose (mg/dl) | 94.7 ± 6.9 | 96.6 ± 7.1 | 97.7 ± 8.8 | 106.1 ± 10.1 |
| 2-h glucose (mg/dl) | 98.2 ± 20.5 | 109.9 ± 16.8 | 109.3 ± 28 | 145.9 ± 32.3 |
| Fasting insulin (µU/ml) | 9.91 ± 6.48 | 11.79 ± 8.83 | 11.0 ± 7.6 | 16.2 ± 9.6 |

*≥20 g/day for women; ≥40 g/day for men

Abbreviations: BP, blood pressure; HDL, high-density lipoprotein; LDL, low-density lipoprotein. Percentages of individuals or means±SD are given for each variable and each group.

Analyses Strategies

It was first screened for significantly differed metabolites concentration among four groups (dT2D, IGT, i-IFG and NGT) for 140 metabolites with cross-sectional studies in KORA S4, and for 131 metabolites in KORA F4. Three IGT-specific metabolites were identified and further investigated in the prospective KORA S4→F4 cohort, to examine whether the baseline metabolite concentrations can predict incident IGT and T2D, and whether they are associated with glucose tolerance seven years later. Our results are based on a prospective population-based cohort, which differed from previous nested case-control study (Wang et al, Nat Med 17: 448-453 (2011)). Also an analysis with same study design was performed using our data. The obtained results provided clues to explain the differences between the two sets of biomarkers.

Identification of Novel Pre-Diabetes Metabolites Distinct from Known T2D Risk Indicators To identify metabolites with altered concentrations between the individuals with NGT, i-IFG, IGT and dT2D, five pairwise comparisons (i-IFG, IGT and dT2D versus NGT, as well as dT2D versus either i-IFG or IGT) were first examined in the cross-sectional KORA S4 survey. Based on multivariate logistic regression analysis, 26 metabolite concentrations differed significantly (P-values<$3.6 \times 10^4$) between two groups in at least one of the five comparisons (FIG. 2A; odds ratios (ORs) and P-values are shown in Table 3). These associations were independent of age, sex, body mass index (BMI), physical activity, alcohol intake, smoking, systolic blood pressure (BP) and HDL cholesterol (Model 1). As expected, the level of total hexose H1, which is mainly represented by glucose (Pearson's correlation coefficient value r between H1 and fasting glucose reached 0.85), was significantly different in all five comparisons. The significantly changed metabolite panel differed from NGT to i-IFG or to IGT. Most of the significantly altered metabolite concentrations were found between individuals with dT2D and IGT as compared to NGT.

To investigate whether HbA1c, fasting glucose and fasting insulin levels mediate the shown associations, these were added as covariates to the regression analysis (model 2) in addition to model 1 (FIG. 2B). We observed that, under these conditions, no metabolite differed significantly when comparing individuals with dT2D to those with NGT, suggesting that these metabolites are associated with HbA1c, fasting glucose and fasting insulin levels. Only nine metabolite concentrations significantly differed between IGT and NGT individuals (Table 3). These metabolites therefore represent novel biomarker candidates and, are independent from the known risk indicators for T2D. The logistic regression analysis was based on each single metabolite, and some of these metabolites are expected to correlate with each other. To further assess the metabolites as a group, two additional statistical methods (the non-parametric random forest and the parametric stepwise selection) were employed to identify unique and independent biomarker candidates. Out of the nine metabolites, five molecules (i.e. glycine, LPC (18:2), LPC (17:0), LPC (18:1) and C2) were selected after random forest, and LPC (17:0) and LPC (18:1) were then removed after the stepwise selection. Thus, three molecules were found to contain independent information: glycine (adjusted OR=0.67 (0.54-0.81), P=$8.6 \times 10^{-5}$), LPC (18:2) (OR=0.58 (0.46-0.72), P=$2.1 \times 10^{-6}$) and acetylcarnitine C2 (OR=1.38 (1.16-1.64), P=$2.4 \times 10^4$) (FIG. 2C). Similar results were observed in the follow-up KORA F4 study. For instance, when 380 IGT individuals were compared with 2134 NGT participants, these three metabolites were also found to be highly significantly different (glycine, OR=0.64 (0.55-0.75), P=$9.3 \times 10^{-8}$; LPC (18:2), OR=0.47 (0.38-0.57), P=$2.1 \times 10^{-13}$; and C2, OR=1.33 (1.17-1.49), P=$4.9 \times 10^{-6}$).

TABLE 3

Odds ratios (ORs) and P-values in five pairwise comparisons with two adjusted models in the KORA S4

| Metabolite | Model 1 | | Model 2 | |
|---|---|---|---|---|
| | OR (95% CI), per SD | P-value | OR (95% CI), per SD | P-value |
| 238 IGT vs. 866 NGT | | | | |
| Glycine | 0.65 (0.53-0.78) | 5.6E-06 | 0.67 (0.54-0.81) | 8.6E-05 |
| LPC (18:2) | 0.58 (0.47-0.7) | 1.3E-07 | 0.58 (0.46-0.72) | 2.1E-06 |
| C2 | 1.37 (1.18-1.59) | 3.8E-05 | 1.38 (1.16-1.64) | 2.4E-04 |
| 91 dT2D vs. 866 NGT | | | | |
| Glycine | 0.47 (0.33-0.65) | 1.1E-05 | 0.44 (0.22-0.83) | 1.6E-02 |
| LPC (18:2) | 0.62 (0.44-0.85) | 4.1E-03 | 0.61 (0.32-1.07) | 1.1E-01 |
| C2 | 1.17 (0.94-1.45) | 1.5E-01 | 1.71 (1.14-2.52) | 6.8E-03 |
| 91 dT2D vs. 234 IGT | | | | |
| Glycine | 0.81 (0.61-1.07) | 1.5E-01 | 0.76 (0.51-1.1) | 1.6E-01 |
| LPC (18:2) | 0.91 (0.69-1.19) | 4.8E-01 | 0.84 (0.57-1.22) | 3.7E-01 |
| C2 | 0.93 (0.71-1.2) | 5.9E-01 | 1.27 (0.87-1.86) | 2.2E-01 |
| 102 i-IFG vs. 866 NGT | | | | |
| Glycine | 0.75 (0.57-0.98) | 3.9E-02 | 0.62 * | 1.0E+00 |
| LPC (18:2) | 0.99 (0.77-1.26) | 9.6E-01 | 0.79 * | 1.0E+00 |
| C2 | 1.2 (0.99-1.46) | 5.9E-02 | 0.18 * | 1.0E+00 |
| 91 dT2D vs. 102 i-IFG | | | | |
| Glycine | 0.62 (0.43-0.87) | 7.8E-03 | 0.62 (0.4-0.93) | 2.5E-02 |
| LPC (18:2) | 0.62 (0.43-0.89) | 1.1E-02 | 0.54 (0.33-0.84) | 8.9E-03 |
| C2 | 0.92 (0.66-1.27) | 6.2E-01 | 1.23 (0.82-1.85) | 3.1E-01 |

* Fasting glucose values were added as co-variants to the model 2, resulting in a perfect separation between i-IFG and NGT.

ORs were calculated with multivariate logistic regression analysis with adjustment for age, sex, BMI, physical activity, alcohol intake, smoking, systolic BP and HDL cholesterol in model 1; model 2 includes those variable in model 1 plus $HbA_{1c}$, fasting glucose and fasting insulin. CI denotes confidence interval.

Predict Risks of IGT and T2D

To investigate the predictive value for IGT and T2D of the three identified metabolites, the associations between baseline metabolite concentrations and incident IGT and T2D were examined using the prospective KORA S4→F4 cohort (Table 2). Baseline metabolite concentrations were compared in 118 incident IGT individuals with 471 NGT control individuals. It was found that glycine and LPC (18:2), but not C2, were significantly different at the 5% level in both adjusted model 1 and model 2 (Table 4). Significant differences were additionally observed for glycine and LPC (18:2), but not for C2, at baseline concentrations between the 91 incident T2D individuals and 785 participants who remained diabetes-free (non-T2D). Each standard deviation (SD) increment of the combinations of the three metabolites was associated with a 33% decreased risk of future diabetes (OR=0.39 (0.21-0.71), P=0.0002). Individuals in the fourth quartile of the combined metabolite concentrations had a three-fold lower chance of developing diabetes (OR=0.33 (0.21-0.52), P=1.8E-05), compared to those whose serum levels were in the first quartile (i.e. combination of glycine, LPC (18:2) and C2), indicating a protective effect from higher concentrations of glycine and LPC (18:2) combined with a lower concentration of C2. With the full adjusted model 2, consistent results were obtained for LPC (18:2) but not for glycine. When the three metabolites were added to the fully adjusted model 2, the area under the receiver-operating-characteristic curves (AUC) increased 2.6% (P=0.015) and 1% (P=0.058) for IGT and T2D, respectively (FIG. 3). Thus, this provides an improved prediction of IGT and T2D as compared to T2D risk indicators.

concentrations with follow-up 2-h glucose values. We found none of them to be associated significantly, indicating that the five amino acids cannot predict risk of IGT. Furthermore, none of these five amino acids showed associations with 2-h glucose values in the cross-sectional KORA S4 study.

TABLE 4

Prediction of IGT and T2D in the KORA cohort

| Model | Glycine | LPC (18:2) | C2 | Glycine, LPC (18:2), C2 |
|---|---|---|---|---|
| A. Metabolite as continuous variable (n = 589) | | | | |
| Per SD | 0.75 (0.58-0.95) | 0.72 (0.54-0.93) | 0.92 (0.73-1.14) | 0.36 (0.20-0.67) |
| P | 0.02 | 0.02 | 0.50 | 0.001 |
| B. Metabolite as categorical variable (n = 589) | | | | |
| 1st quartile | 1.0 (reference) | 1.0 (reference) | 1.0 (reference) | 1.0 (reference) |
| 2nd quartile | 1.0 (0.80-1.46) | 0.96 (0.73-1.27) | 0.89 (0.66-1.23) | 0.54 (0.30-0.97) |
| 3rd quartile | 1.0 (0.74-1.34) | 0.71 (0.51-0.99) | 0.93 (0.69-1.26) | 0.66 (0.37-1.18) |
| 4th quartile | 0.78 (0.55-1.06) | 0.78 (0.54-1.12) | 0.99 (0.73-1.35) | 0.36 (0.19-0.69) |
| P for trend | 0.06 | 0.05 | 0.79 | 0.0082 |
| C. Metabolite as continuous variable (n = 876) | | | | |
| Per SD | 0.73 (0.55-0.97) | 0.70 (0.51-0.94) | 0.94 (0.74-1.18) | 0.39 (0.21-0.71) |
| P | 0.04 | 0.02 | 0.59 | 0.0002 |
| D. Metabolite as categorical variable (n = 876) | | | | |
| 1st quartile | 1.0 (reference) | 1.0 (reference) | 1.0 (reference) | 1.0 (reference) |
| 2nd quartile | 0.87 (0.71-1.07) | 0.95 (0.77-1.17) | 1.05 (0.85-1.31) | 0.50 (0.33-0.76) |
| 3rd quartile | 0.82 (0.67-1.01) | 0.70 (0.56-0.88) | 0.97 (0.78-1.19) | 0.57 (0.38-0.88) |
| 4th quartile | 0.67 (0.54-0.84) | 0.68 (0.54-0.88) | 1.21 (0.98-1.50) | 0.33 (0.21-0.52) |
| P for trend | 0.00061 | 0.00021 | 0.19 | 1.8E−05 |
| E. Linear regression (n = 843) | | | | |
| β estimates* (95% CI) | −2.47 (−4.64, −0.29) | −4.57 (−6.90, −2.24) | 1.02 (−1.11, 3.15) | −4.23 (−6.52, −2.31) |
| P | 0.026 | 0.00013 | 0.59 | 8.8E−05 |

*β estimate indicates the future difference in the glucose tolerance corresponding to the one SD differences in the normalized baseline metabolite concentration.

Odds ratios (ORs, 95% confidence intervals) and P-values of multivariate logistic regression results are shown in (A) and (B) for IGT, and in (C) and (D) for T2D, respectively, whereas β estimates and P-values from linear regression analysis between metabolite concentration in baseline KORA S4 and 2-h glucose values in follow-up KORA F4 are shown in (E). All models were adjusted for age, sex, BMI, physical activity, alcohol intake, smoking, systolic BP and HDL cholesterol.

Baseline Metabolite Concentrations Correlate with Future Glucose Tolerance

Next investigated were the associations between baseline metabolite concentrations and follow-up 2-h glucose values after an oral glucose tolerance test. Consistent results were observed for the three metabolites: glycine and LPC (18:2), but not acetylcarnitine C2 levels, were found to be significantly associated, indicating that glycine and LPC (18:2) predict glucose tolerance. Moreover, the three metabolites (glycine, LPC (18:2) and C2) revealed high significance even in the fully adjusted model 2 in the cross-sectional KORA S4 cohort. As expected, a very significant association ($P=1.5\times10^{-22}$) was observed for hexose H1 in model 1, while no significance (P=0.12) was observed for it in the fully adjusted model 2.

Prospective Population-Based Versus Nested Case-Control Designs

To investigate the predict value of the five branched-chain and aromatic amino acids (isoleucine, leucine, valine, tyrosine and phenylalanine) (Wang et al, Nat Med 17: 448-453 (2011)) in our study, we correlated the baseline metabolite concentrations with follow-up 2-h glucose values. We found none of them to be associated significantly, indicating that the five amino acids cannot predict risk of IGT. Furthermore, none of these five amino acids showed associations with 2-h glucose values in the cross-sectional KORA S4 study.

To replicate the identified five branched-chain and aromatic amino acids (Wang et al, 2011), the baseline samples were matched to the 91 incident T2D using the same method described previously (Wang et al, Nat Med 17: 448-453 (2011)). We replicated four out of the five branched-chain and aromatic amino acids. As expected, the three identified IGT-specific metabolites did not significantly differ between the matched case control samples, because the selected controls were enriched with individuals accompanied by high-risk features such as obesity and elevated fasting glucose as described by Wang et al (Wang et al, Nat Med 17: 448-453 (2011)). In fact, the 91 matched controls include about 50% pre-diabetes individuals, which is significantly higher than the general population (about 15%).

The invention claimed is:

1. A method of identifying a predisposition for developing type 2 diabetes mellitus in a subject, said method comprising the step of measuring in a sample obtained from said subject the amount of at least four metabolites comprising:
   (a) a first group comprising the metabolites glycine, lysoPhosphatidylcholine acyl C18:2, and phosphatidylcholine acyl-alkyl C34:2; and
   (b) a second group comprising the metabolite acetylcarnitine C2; and
   optionally, preparing a hard or soft copy comprising values of amounts of metabolites determined; and
   wherein a decrease in the amount of glycine, lysoPhosphatidylcholine acyl C18:2, and phosphatidylcholine acyl-alkyl C34:2, and an increase in the amount of acetylcarnitine C2 as compared to the amount of the corresponding metabolites of a control is indicative of a predisposition to develop type 2 diabetes mellitus.

2. The method of claim 1, wherein the amount the metabolites of the first group being decreased compared to the amount of the metabolites in the control is measured in a subject prior to the subject exhibiting an increase in blood glucose levels.

3. The method of claim 1, wherein the method is performed at least every two years.

4. The method of claim 1 wherein the first group further comprises lysoPhosphatidylcholine acyl C17:0, and at least four metabolites of the first group are measured.

5. The method of claim 1, wherein said sample comprises blood, serum or plasma.

6. The method of claim 1, wherein the amount of the metabolites is measured using targeted or non-targeted NMR, FIA-MS, GC-MS or LC-MS.

7. The method of claim 1, wherein the amount of acetylcarnitine C2 being increased compared to the amount of acetylcarnitine C2 in the control is measured in a subject prior to the subject exhibiting an increase in blood glucose levels.

* * * * *